(12) United States Patent
Schwarz et al.

(10) Patent No.: US 7,189,754 B2
(45) Date of Patent: Mar. 13, 2007

(54) PYRROLIDINE ESTER DERIVATIVES WITH OXYTOCIN MODULATING ACTIVITY

(75) Inventors: Matthias Schwarz, Thonex (CH); Anna Quattropani, Geneva (CH); Alexander Scheer, Versoix (CH); Jerome Dorbais, Annecy (FR); Vincent Pomel, Groisy (FR)

(73) Assignee: Applied Research Systems ARS Holding NV, Curacao (AN)

( * ) Notice: Subject to any disclaimer, the term of this patent is extended or adjusted under 35 U.S.C. 154(b) by 334 days.

(21) Appl. No.: 10/471,290

(22) PCT Filed: Mar. 19, 2002

(86) PCT No.: PCT/EP02/03005

§ 371 (c)(1), (2), (4) Date: Feb. 23, 2004

(87) PCT Pub. No.: WO02/074741

PCT Pub. Date: Sep. 26, 2002

(65) Prior Publication Data

US 2004/0147511 A1 Jul. 29, 2004

(30) Foreign Application Priority Data

Mar. 20, 2001 (EP) .................................. 01106888

(51) Int. Cl.
A61K 31/40 (2006.01)
C07D 207/00 (2006.01)
(52) U.S. Cl. ........................ 514/423; 548/533; 548/532
(58) Field of Classification Search ................ 548/533, 548/532; 514/423
See application file for complete search history.

(56) References Cited

U.S. PATENT DOCUMENTS 5,481,005 A * 1/1996 Wagnon et al. ............. 548/537
5,756,497 A 5/1998 Bell et al.
5,780,471 A 7/1998 Venkatesan et al.
2004/0147511 A1 7/2004 Schwarz et al.

FOREIGN PATENT DOCUMENTS

WO 96/22775 8/1996
WO 99 41757 10/1999
WO 99 52868 10/1999

OTHER PUBLICATIONS

Caprariis et al., Journal of Heterocyclic Chem., 1989, 26:1023-27.*
Robert M. Adlington et al.: "A radical route to 2(S)-4-exomethylene proline" TETRAHEDRON, vol. 48, No. 31, pp. 6529-6536.
Elizabeth M. Smith et al.: "Synthesis and Pharmacological activity of angiotensin converting enzyme inhibitors: N-(mercaptoacy)-4-substituted-(S)-prolines" Journal of Medicinal Chemistry, vol. 31, No. 4, pp. 85-885, 1988.

Sharad Kumar Panday et al.: "A short and efficient synthesis of (S)-4-methylene proline benzyl ester from (S)-pyroglutamic acid" Tetrahedron Letters, vol. 35, No. 36, pp. 6673-6676 1994.
RM Adlington et al.: "A radical route to 2(S)-4-exomethylene proline" TETRAHEDRON, vol. 48, No. 31, pp. 6529-6536 1992.
EM Smith et al.: "Synthesis and pharmacological activity of angiotensin converting enzyme inhibitors: N-(mercaptoacyl)-4-substituted-(S)-prolines" Journal of Medicinal Chemistry, vol. 31, No. 4, pp. 85-885, 1998.
SR Panday et al.: "A short oand efficient synthesis of (S)-4-methylene proline benzyl ester from (S)-pyroglutamic acid" Tetrahedron Letters, vol. 35, No. 36, pp. 6673-6676 1994.
Maggi et al. J. Clin. Endocrinol. Metabol., vol. 70, No. 4, pp. 1142-1154 1990.
Evans et al. J. Med. Chem., vol. 35, pp. 3919-3927.
U.S. Appl. No. 11/449,802, filed Jun. 9, 2006, Schwarz et al.
Cook, N., et al., "SPA: A Revolutionary New Technique for Drug Screening," Phamaceutical Manufacturing International, 1992, pp. 49-53.

(Continued)

*Primary Examiner*—Joseph K. McKane
*Assistant Examiner*—Rei-tsang Shiao
(74) *Attorney, Agent, or Firm*—Oblon, Spivak, McClelland, Maier & Neustadt, P.C.

(57) ABSTRACT

The present invention is related to the use of pyrrolidine esters of formula (I) for the treatment and/or prevention of premature labor, premature birth and dysmenorrhea. In particular, the present invention is related to the use of pyrrolidine esters of formula (I) to modulate, notably to antagonize the oxytocin receptor. The present invention is furthermore related to novel pyrrolidine esters. X is selected from the group consisting of $CR^6R^7$, $NOR^6$, $NNR^6R^7$; R is selected from the group comprising or consisting of $C_1$–$C_6$ alkyl, $C_2$–$C_6$ alkenyl, $C_2$–$C_6$ alkynyl, saturated or unsaturated 3–8-membered cycloalkyl which may contain 1 to 3 heteroatoms selected of N, O, S, aryl, heteroaryl, $C_1$–$C_6$-alkyl aryl, $C_1$–$C_6$-alkyl heteroaryl. $R^1$ is selected from the group comprising or consisting of $C_1$–$C_6$-alkyl, $C_2$–$C_6$-alkenyl, $C_2$–$C_6$-alkynyl, aryl, heteroaryl, 3–8-membered cycloalkyl, acyl, $C_1$–$C_6$-alkyl aryl, $C_1$–$C_6$-alkyl heteroaryl, said cycloalkyl or aryl or heteroaryl groups may be fused with 1–2 further cycloalkyl or aryl or heteroaryl group

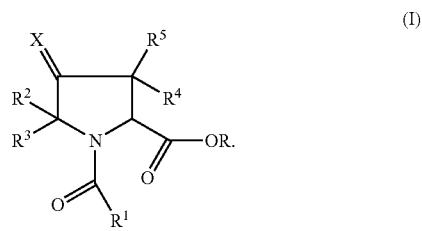

(I)

19 Claims, No Drawings

OTHER PUBLICATIONS

Breitmaier, E., et al., "High-Resolution Methods and Applications in Organic Chemistry and Biochemistry," Carbon-13 NMR Spectroscopy, 3rd Edition, VCH, 1987, pp. 240-241.

Mitchell, B. F., "The Oxytocin and its Receptor in the Process of Parturition," Journal of the Society for Gynecologic Investigation, 2001, 8, pp. 122-133.

Gimpl, G., et al., "The Oxytocin Receptor System; Structure, Function, and Regulation," Physiological Reviews, 2001, 81, pp. 629-683.

Jarowicki, K., et al., "Protecting Groups," J. Chem. Soc., Perkin Trans., 1, 1999, pp. 1589-1615.

Nelson, T. D., et al., "Selective Deprotection of Silyl Ethers," Synthesis, 1996, pp. 1031-1069.

Kocienski, P. J., "Protecting Groups," Foundations of Organic Chemistry Series, pp. 1-260, 1994.

* cited by examiner

PYRROLIDINE ESTER DERIVATIVES WITH OXYTOCIN MODULATING ACTIVITY

This application is a 371 of PCT/EP02/3005 filed on Mar. 19, 2002.

FIELD OF THE INVENTION

The present invention is related to the use of pyrrolidine esters of formula (I) for the treatment and/or prevention of premature labor, premature birth and dysmenorrhea. In particular, the present invention is related to the use of pyrrolidine esters of formula (I) to modulate, notably to antagonise, the oxytocin receptor. The present invention is furthermore also related to novel pyrrolidine esters.

BACKGROUND OF THE INVENTION

Oxytocin (OT) is a peptide hormone and causes the contraction of the uterus of mammals during labor. The corresponding oxytocin receptor belongs to the family of G-protein-coupled receptors and is similar to $V_{1a}$ and $V_2$ vasopressin receptors. OT receptors increase dramatically during the course of pregnancy. The concentration of OT receptors has been shown to correlate with spontaneous uterine activity (M. Maggi et al. *J. Clin. Endocrinol Metabol;* 70; 1142, 1990). Premature labor, though, and premature birth is undesired as it represents a major cause of perinatal morbidity and mortality. Hence, the management of preterm labor represents a significant problem in the field of obstetrics.

In recent years, strong evidence has accumulated indicating that the hormone oxytocin plays a major role in initiating labor in mammals, notably in humans. Thereby, it is assumed that oxytocin exerts said effect in a direct as well as an indirect way, by contracting the uterine myometrium and by enhancing the synthesis and release of contractile prostaglandins from the uterine endometrium/decidua. These prostaglandins may further-more play a role in the cervical ripening process. This "up-regulation" of oxytocin receptors and increased uterine sensitivity seems to be due to trophic effects of rising plasma levels of estrogen towards term. By down-regulating oxytocin, it is expected that both the direct (contractile) and indirect (increased prostaglandin synthesis) effects of oxytocin on the uterine could be blocked. An oxytocin modulator, e.g. blocker or antagonists would likely be more efficacious for treating preterm labor than current regimens. Moreover, as oxytocin at term has only an effect on the uterus, such an oxytocin modulator would have only few or no side efect.

A further condition being related to oxytocin is dysmenorrhea, which is characterised by cyclic pain associated with menses during ovulatory cycles. Said pain is believed to result from uterine contractions and ischemia, probably mediated by the effect of prostaglandins produced in the secretory endometrium. By blocking both the indirect and direct effects of oxytocin on the uterus, an oxytocin antagonist is believed more efficacious for treating dysmenorrhea than current regimens.

Some agents counteracting the action of oxytocin (OT) are currently used in clinical studies. Such tocolytic agents (i.e. uterine-relaxing agents) include beta-2-adrenergic agonists, magnesium sulfate and ethanol. The leading beta-2-adrenergic agonists is Ritodrine, which causes a number of cardiovascular and metabolic side effects, including tachycardia, increased renin secretion, hyperglycemia and reactive hypoglycemia in the infant. Further beta-32-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

The principal drawback to the use of peptide antagonists including also atosiban is the problem of low oral bioavailability resulting from intestinal degradation. Hence, they are administered parenterally.

The development of non-peptide ligands for peptide hormone receptors are expected to overcome this problem. The first to report small molecule selective oxytocin antagonists was Merck. Apart from cyclic hexapeptides, Merck suggested indanylpiperidines and tolylpiperazines as orally deliverable OT antagonists (Evans et al. *J. Med. Chem.,* 35, 3919 (1992). In WO 96/22775 and U.S. Pat. No. 5,756,497 Merck reported benzoxazinylpiperidines or benzoxazinones as OT receptor antagonists.

The objective of this invention is to provide substances which more effectively down-regulate—up to antagonizing—the function of OT in disease states in animals, preferably mammals, especially in humans. It is another purpose of this invention to provide a method of antagonizing the functions of oxytocin in disease states of mammals. It is also an objective of the present invention to provide small molecule chemical compounds for the modulation, preferably the down-regulation or even antagonisation of the oxytocin receptor. Moreover, it is an objective of the present invention to provide methods for preparing said small molecule chemical compounds. It is furthermore an objective of the present invention to provide a new category of pharmaceutical formulations for the treatment of preterm labor and dysmenorrhea, and/or diseases mediated by the oxytocin receptor. It is finally an objective of the present invention to provide a method of treating and/or preventing disorders mediated by the oxytocin receptor, like preterm labor and dysmenorrhea by antagonising the binding of oxytocin to its receptor.

SUMMARY OF THE INVENTION

The present invention relates to use of pyrrolidine esters of formula (I) for the treatment and/or prevention of premature labor, premature birth and dysmenorrhea. In particular, the present invention is related to the use of pyrrolidine esters of formula (I) to modulate, notably to antagonise the oxytocin receptor. The present invention is furthermore related to novel pyrrolidine esters.

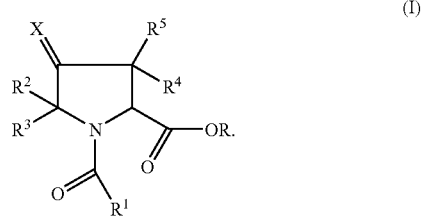

(I)

DETAILED DESCRIPTION OF THE INVENTION

The aforementioned objectives have been met according to the independent claims. Preferred embodiments are set out within the dependent claims which are incorporated herein.

The following paragraphs provide definitions of the various chemical moieties that make up the compounds according to the invention and are intended to apply uniformly throughout the specification and claims unless an otherwise expressly set out definition provides a broader definition.

"$C_1$–$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$–$C_6$-alkyl aryl" refers to $C_1$–$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$–$C_6$-alkyl heteroaryl" refers to $C_1$–$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (allyl, —CH$_2$CH=CH$_2$) and the like.

"Alkynyl" refers to alkynyl groups preferably having from 2 to 6 carbon atoms and having at least 1–2 sites of alkynyl unsaturation, preferred alkynyl groups include ethynyl (—C≡CH), propargyl (—CH$_2$C≡CH), and the like.

"Acyl" refers to the group —C(O)R where R includes H, "$C_1$–$C_6$-alkyl", "aryl", "heteroaryl", "$C_1$–$C_6$-alkyl aryl" or "$C_1$–$C_6$-alkyl heteroaryl".

"Acyloxy" refers to the group —OC(O)R where R includes H, "$C_1$–$C_6$-alkyl", "aryl", "hetero-aryl", "$C_1$–$C_6$-alkyl aryl" or "$C_1$–$C_6$-alkyl heteroaryl".

"Alkoxy" refers to the group —O—R where R includes "$C_1$–$C_6$-alkyl" or "aryl" or "heteroaryl" or "$C_1$–$C_6$-alkyl aryl" or "$C_1$–$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$–$C_6$-alkyl" or "aryl" or "heteroaryl" or "$C_1$–$C_6$-alkyl aryl" or "$C_1$–$C_6$-alkyl heteroaryl".

"Aminocarbonyl" refers to the group —C(O)NRR$^1$ where each R, R' includes independently hydrogen or $C_1C_6$-alkyl or aryl or heteroaryl or "$C_1$–$C_6$-alkyl aryl" or "$C_1$–$C_6$-alkyl heteroaryl".

"Acylamino" refers to the group —NR(CO)R' where each R, R' is independently hydrogen or "$C_1$–$C_6$-alkyl" or "aryl" or "heteroaryl" or "$C_1$–$C_6$-alkyl aryl" or "$C_1$–$C_6$-alkyl heteroaryl".

"Halogen" refers to fluoro, chloro, bromo and iodo atoms.

"Sulfonyl" refers to group "—SO$_2$—R" wherein R is selected from H, "aryl", "heteroaryl", "$C_1$–$C_6$-alkyl", "$C_1$–$C_6$-alkyl" substituted with halogens e.g. an —SO$_2$—CF$_3$ group, "$C_1$–$C_6$-alkyl aryl" or "$C_1$–$C_6$-alkyl heteroaryl".

"Sulfoxy" refers to a group "—S(O)—R" wherein R is selected from H, "$C_1$–$C_6$-alkyl", "$C_1$–$C_6$-alkyl" substituted with halogens e.g. an —SO—CF$_3$ group, "aryl", "heteroaryl", "$C_1$–$C_6$-alkyl aryl" or "$C_1$–$C_6$-alkyl heteroaryl".

"Thioalkoxy" refers to groups —S—R where R includes "$C_1$–$C_6$-alkyl" or "aryl" or "heteroaryl" or "$C_1$–$C_6$-alkyl aryl" or "$C_1$–$C_6$-alkyl heteroaryl". Preferred thioalkoxy groups include thiomethoxy, thioethoxy, and the like.

"Substituted or unsubstituted": Unless otherwise constrained by the definition of the individual substituent given in the present specification, the above set out groups, like "alkyl", "alkenyl", "alkynyl", "aryl" and "heteroaryl" etc. groups may optionally be substituted with from 1 to 5 substituents selected from the group consisting of "$C_1$–$C_6$-alkyl", "$C_1$–$C_6$-alkyl aryl", "$C_1$–$C_6$-alkyl heteroaryl", "$C_2$–$C_6$-alkenyl", "$C_2$–$C_6$-alkynyl", primary, secondary or tertiary amino groups or quarternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula (I) that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR,R',R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded. In the absence of an asymmetric synthesis, racemic products are usually obtained that do however also have the inventive set out activity as OT-R antagonists.

It was now found that pyrrolidine ester derivatives according to formula (I) are useful for the treatment and/or prevention of preterm labor, premature birth and dysmenorrhea of mammals and in particular of humans. Specifically, the pyrrolidine ester derivatives according to formula (I) are useful for the treatment and/or prevention of disorders-related to the oxytocin function, i.e. disorders that are mediated by the oxytocin receptor. Preferably, the compounds of formula (I) are suitable to modulate, in particular to down-regulate the OT-R function and more specifically to antagonise the oxytocin receptor. When the oxytocin receptor is bound by the compounds according to formula (I), oxytocin is antagonised by being blocked from its receptor and is therefore unable to exert its biologic or pharmacological effects.

The compounds being suitable for the treatment and/or prevention of preterm labor, premature birth and dysmenorrhea are those of formula (I).

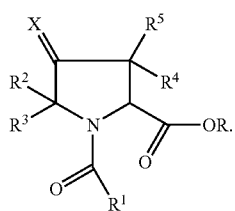

(I)

Formula (I) also comprises geometrical isomers, optically active forms like enantiomers, diastereomers and racemate forms, as well as pharmaceutically acceptable salts thereof.

Preferred pharmaceutically acceptable salts of the compound I, are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

In said formula (I), X is selected from the group consisting of $CR^6R^7$, $NOR^6$, $NNR^6R^7$.

R is selected from the group comprising or consisting of unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–8-membered-cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, unsubstituted or substituted $C_1$–$C_6$-alkyl heteroaryl.

$R^1$ is selected from the group comprising or consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, acyl, unsubstituted or substituted $C_1$–$C_6$-alkyl aryl, unsubstituted or substituted $C_1$–$C_6$-alkyl heteroaryl, said cycloalkyl or aryl or heteroaryl groups may be fused with 1–2 further cycloalkyl or aryl or heteroaryl group.

$R^2$, $R^3$, $R^4$ and $R^5$ are independently selected from each other from the group consisting of hydrogen, halogen, $C_1$–$C_6$-alkyl. Preferably they are all hydrogen.

$R^6$ and $R^7$ are independently selected from the group comprising or consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, unsubstituted or substituted $C_1$–$C_6$-alkyl heteroaryl.

Alternatively, $R^6$, $R^7$ could form together with the N atom to which they are attached a 3–8 membered substituted or unsubstituted, saturated or unsaturated heterocyclic ring which may contain 1–2 further heteroatoms selected from N, S and O and which is optionally fused with an aryl, heteroaryl or 3–8 membered saturated or unsaturated cycloalkyl ring.

Compounds of formula (I)—wherein R is H or alkyl—are disclosed in WO 99/52868. The compounds claimed therein are said to be inhibitors of metalloproteases.

Preferred pyrrolidine derivatives are those compounds according to formula (I) wherein R is an unsubstituted or substituted $C_1$–$C_6$ alkyl.

Particularly preferred pyrrolidine derivatives are those compounds according to formula (I) wherein X is $NOR^6$, and $R^6$ is selected from the group consisting of H, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted acyl, unsubstituted or substituted aryl, unsubstituted or substituted heteroaryl, unsubstituted or substituted saturated or unsaturated 3–8-membered cycloalkyl, unsubstituted or substituted $C_1$–$C_6$-alkyl aryl, unsubstituted or substituted $C_1$–$C_6$-alkyl heteroaryl, said cycloalkyl or aryl or heteroaryl groups may be fused with 1–2 further cycloalkyl or aryl or heteroaryl groups. Particularly preferred $R^6$ is H or $CH_3$.

More preferred groups $R^1$ are substituted or unsubstituted $C_1$–$C_6$-alkyl, substituted or unsubstituted $C_2$–$C_6$-alkenyl, unsubstituted or substituted $C_2$–$C_6$-alkynyl, substituted or unsubstituted aryl, substituted or unsubstituted heteroaryl, saturated or unsaturated 3–8-membered substituted or unsubstituted cycloalkyl and still more preferred $R^1$ are substituted or unsubstituted $C_1$–$C_6$-alkyl or substituted or unsubstituted aryl. A particularly preferred substituent $R^1$ is a substituted or unsubstituted biphenyl.

According to a most preferred embodiment, the pyrrolidine derivatives according to formula I are those wherein X is $NOR^6$, $R^6$ is H, a $C_1$–$C_6$-alkyl, e.g. a methyl group, or aryl or $C_1$–$C_6$-alkyl aryl group and $R^1$ is a $C_1$–$C_6$-alkyl or aryl or $C_1$–$C_6$-alkyl aryl group. Even more preferred are those pyrrolidine derivatives, wherein X is $NOR^6$, $R^6$ is methyl, R is an unsubstituted or substituted $C_1$–$C_6$-alkyl group, e.g. a methyl group and $R^1$ is a substituted or unsubstituted biphenyl.

The compounds of formula (I) may contain one or more asymmetric centers and may therefore exist as enantiomers or diastereoisomers. It is to be understood that the invention includes both mixtures and separate individual isomers or enantiomers of the compounds of formula (I). In a particularly preferred embodiment the pyrrolidine derivatives according to formula (I) are obtained in an enantiomeric excess of at least 52% ee, preferably of at least 92–98% ee. Also, E/Z isomers with regard to pyrrolidine derivatives having residues X being =CR$^6$R$^7$ whereby both R$^6$R$^7$ are different from each other, and/or with regard to pyrrolidine derivatives having residues X being =NOR$^6$ or =NNR$^6$R$^7$ are comprised by the present invention.

A further aspect of the present invention is related to the use of the pyrrolidine derivatives according to formula (I) for the preparation of pharmaceutical compositions for the treatment and/or prevention of premature labor, premature birth, for stopping labor prior to cesarean delivery and dysmenorrhea. Preferably, the compounds according to formula (I) are suitable for the modulation of the OT function, thus specifically allowing the treatment and/or prevention of disorders which are mediated by the oxytocin receptor. Said treatment involves the modulation—notably the down regulation or the antagonisation—of the oxytocin receptor.

Still a further aspect of the present invention is related to the actually novel pyrrolidine compounds of formula (I). Said compounds have the formula (I')

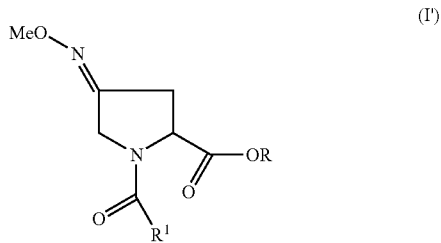

(I')

In formula (I'), R is selected from C$_1$–C$_6$ alkyl, C$_1$–C$_6$ alkyl aryl, C$_1$–C$_6$ alkyl heteroaryl, 3–8-membered cycloalkyl. R$^1$ is selected from an unsubstituted or substituted 1,1'-biphenyl, pyridinyl-phenyl or pyrimidinyl-phenyl group.

More preferred is R being a C$_1$–C$_4$ alkyl, i.e. a methyl, ethyl, propyl or butyl or group, most preferred a methyl group.

More preferred R$^1$ is a 1,1'-biphenyl group which is substituted by 1 or 2 moieties selected from the group consisting of C$_1$–C$_6$ alkyl, C$_1$–C$_6$ alkoxy, halogen, CN. Most preferred is a methyl group.

Specific compounds of formula (I') are the following:

Methyl (2S,4EZ)-4-(methoxyimino)-1-[(2'-methyl[1,1'-biphenyl]-4-yl)carbonyl]-2-pyrrolidinecarboxylate Methyl (2S,4EZ)-1-([1,1'-biphenyl]-4-ylcarbonyl)-4-(methoxyimino)-2-pyrrolidinecarboxylate Methyl (2S,4E)-4-(methoxyimino)-1-[(2'-methyl[1,1'-biphenyl]4-yl)carbonyl]-2-pyrrolidinecarboxylate Methyl (2S,4Z)-4-(methoxyimino)-1-[(2'-methyl[1,1'-biphenyl]-4-yl)carbonyl]-2-pyrrolidinecarboxylate Methyl (2S,4EZ)-1-[(2'-fluoro[1,1'-biphenyl]-4-yl)carbonyl]-4-(methoxyimino)-2-pyrrolidinecarboxylate Methyl (2S,4)-1-[(2'-fluoro[1,1'-biphenyl]-4-yl)carbonyl]-4-(methoxyimino)-2-pyrrolidinecarboxylate Methyl (2S,4EZ)-1-[(2'-chloro[1,1'-biphenyl]-4-yl)carbonyl]-4-(methoxyimino)-2-pyrrolidinecarboxylate Methyl (2S,4EZ)-1-[(2'-cyano[1,1'-biphenyl]-4-yl)carbonyl]-4-(methoxyimino)-2-pyrrolidinecarboxylate Methyl (2S,4EZ)-4-(methoxyimino)-1-{[2-(trifluoromethyl)[1,1'-biphenyl]-4-yl]carbonyl}-2-pyrrolidinecarboxylate Methyl (2S,4EZ-1-[(2'-methoxy[1,1'-biphenyl]-4-yl)carbonyl]-4-(methoxyimino)-2-pyrrolidinecarboxylate Methyl (2S,4EZ)-1-[(2',6'-dimethyl[1,1'-biphenyl]-4-yl)carbonyl]-4-(methoxyimino)2-pyrrolidinecarboxylate Methyl (2S,4EZ)-1-[(2',3-dimethyl[1,1'-biphenyl]-4-yl)carbonyl]-4-(methoxyimino)-2-pyrrolidinecarboxylate Methyl (2S,4EZ)-1-[(3-methyl[1,1'-biphenyl]-4-yl)carbonyl]-4-(methoxyimino)-2-pyrrolidinecarboxylate Methyl (2S,4EZ)-1-[(3',4'-dichloro[1,1'-biphenyl]-4-yl)carbonyl]-4-(methoxyimino)2-pyrrolidinecarboxylate Ethyl (2S,4EZ)-1-([1,1'-biphenyl]-4-ylcarbonyl)-4-(methoxyimino)-2-pyrrolidinecarboxylate sec-butyl (2S,4EZ)-4-(methoxyimino)-1-[(2'-methyl[1,1'-biphenyl]-4-yl)carbonyl]-2-pyrrolidinecarboxylate Cyclopentyl (2S,4EZ)-4-(methoxyimino)-1-[(2'-methyl[1,1'-biphenyl]-4-yl)carbonyl]-2-pyrrolidinecarboxylate Methyl (2S,4EZ)-1-[(4'-fluoro[1,1'-biphenyl]-4-yl)carbonyl]-4-(methoxyimino)-2-pyrrolidinecarboxylate Methyl (2S,4EZ)-4-(methoxyimino)-1-[4-(5-pyrimidinyl)benzoyl]-2-pyrrolidinecarboxylate Methyl (2S,4EZ)-4-(methoxyimino)-1-[4-(2-pyridinyl)benzoyl]-2-pyrrolidinecarboxylate Methyl (2S,4EZ)-4-(methoxyimino)-1-[4-(3-methyl-2-pyridinyl)benzoyl]-2-pyrrolidinecarboxylate The pyrrolidine derivatives exemplified in this invention can be prepared from readily available starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Generally, the pyrrolidine derivatives according to the general formula (I) could be obtained by several processes, using both solution-phase and solid-phase chemistry protocols. Depending on the nature of the R- and X-moieties, certain synthtic approaches will, in some instances, be preferred over others, and it is assumed that the choice of the most suitable process will be evident to the practitioner skilled in the art.

According to one process, pyrrolidine derivatives according to the general formula (I), whereby the substituents X, R and R$^{1-5}$ are as above defined, are prepared from the corresponding suitably N-protected 4-substituted pyrrolidine derivatives II, whereby the substituents X, R and R$^{1-5}$ are as above defined, by solution-phase chemistry protocols such as described in the Examples and shown in Scheme 1, below. Removal of the N-protecting group of II, using an appropriate deprotection agent (e.g. TFA, piperidine, H$_2$/Pd/C) under standard conditions for N-deprotection well known to the person skilled in the art, produces derivatives of formula (III). These can be treated with acylating agents of general formula (IV), whereby the substituent R$^1$ is as above defined, while Y could be any appropriate leaving group. Preferred acylating agents IV are acid chlorides (IVa), used in conjunction with a tertiary amine base, or carboxylic acids (IVb), used in conjunction with an appropriate peptide coupling agents, such as e.g. DIC, EDC, TBTU, DECP, or others, to yield the pyrrolidine ester products of general formula (I), with X, R and R$^{1-5}$ being as above defined.

Scheme 1

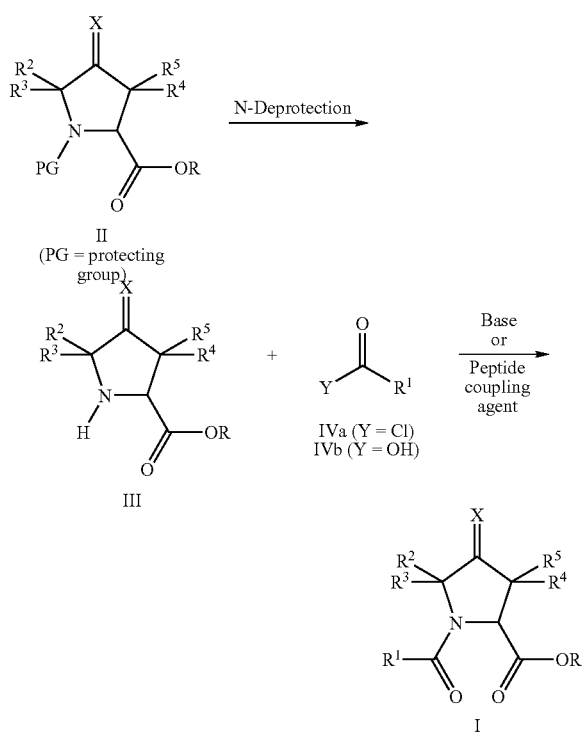

Pyrrolidine ester compounds of formula (II), whereby the substituents X, R and R$^{1-5}$ are as above defined, are obtained from the corresponding pyrrolidine carboxylic acids V, and alcohols VI, according to any of the standard methods well know to the person skilled in the art for transforming a carboxylic acid into an ester, e.g. those described in the Examples and shown in Scheme 2. The choice of the best reagent and reaction conditions will depend on the nature of the X- and R-groups, and of the N-protection group, as will be obvious to the practitioner skilled in the art.

Scheme 2

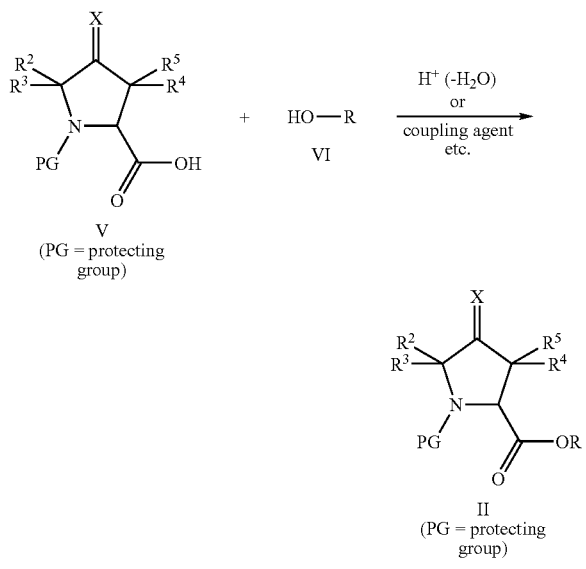

Intermediate compounds of formula V, whereby the substituent X is CR$^6$R$^7$, and R$^6$ and R$^7$ are as above defined (i.e. compounds of formula Va), may be prepared from compounds of general formula VI by Wittig-type reactions with anions of phosphoranes such as VIIa and/or of phosphonates such as VIIb, followed by saponification of the ester function using standard synthetic techniques, as hereinafter described in the Examples and shown in scheme 3.

Scheme 3

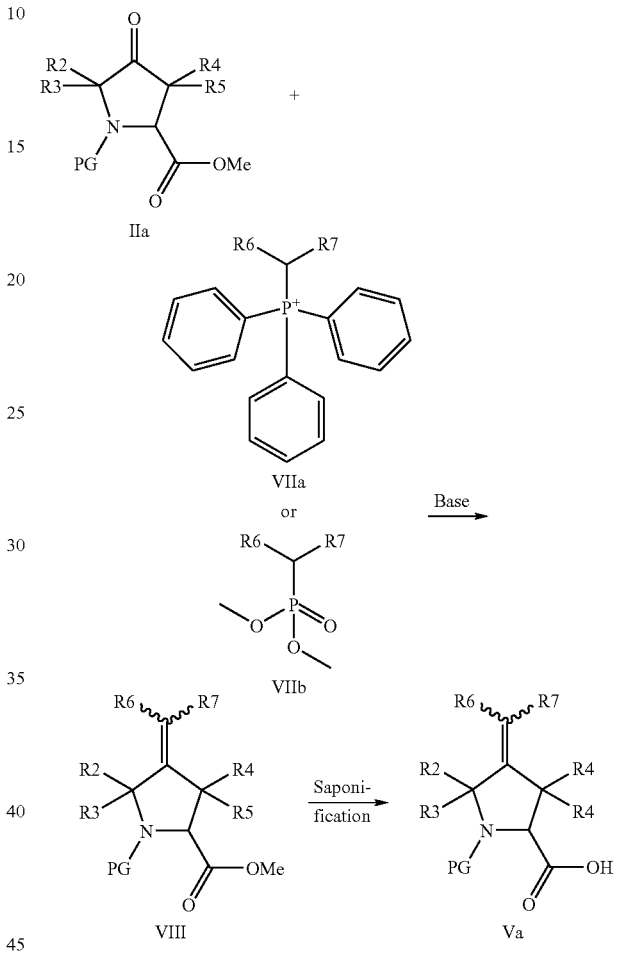

Intermediate compounds of formula V, wherein the substituent X is NOR$^6$ or NNR$^6$R$^7$, and R$^6$ and R$^7$ are as above defined (i.e. compounds of formula Vb and Vc), may be prepared from compounds of general formula (IX) by reaction with substituted hydroxylamines Xb and/or substituted hydrazines and/or hydrazides Xc using standard synthetic techniques as hereinafter described in the Examples and shown in Scheme 4. Compounds of formula Xa are commercially available or prepared by standard synthetic techniques as hereinafter described in the Examples.

Scheme 4

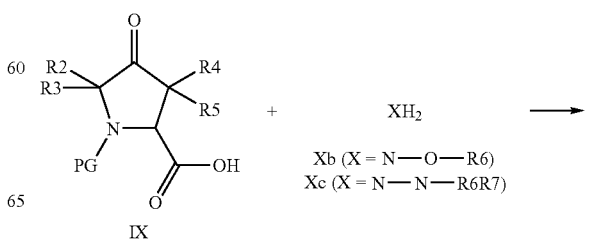

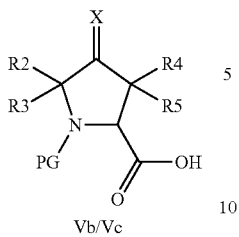

Vb/Vc

The intermediate compounds of general formulae VI and/or IX may be prepared from commercially available, suitably N-protected (e.g. Boc) 4-hydroxyprolines XI, by a reaction sequence consisting of oxidation and, if appropriate, methylation, using standard synthetic techniques as hereinafter described in the Examples and illustrated in Scheme 5.

Scheme 5

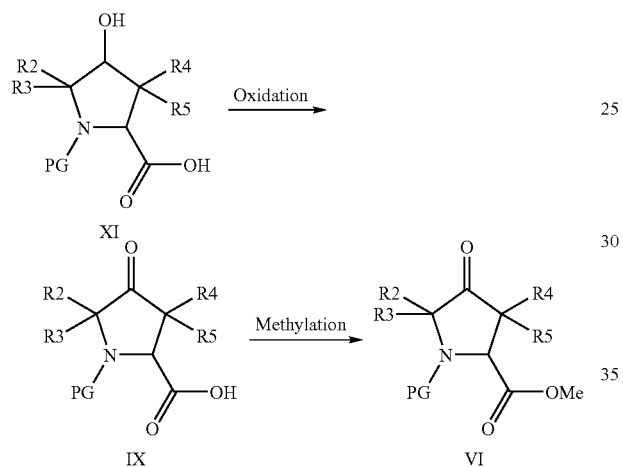

A further, alternative approach of preparing the compounds of the present invention is depicted in Scheme 6. Following to this process the pyrrolidine derivatives—whereby the substituents X, R and $R^{1-5}$ are as above defined—are prepared from compounds of formula XII, using the synthetic techniques as outlined in Schemes 3 and 4. As further shown in Scheme 6, compounds of formula XII may be obtained from compounds of formula (Ia) through transformation of the methyloxime into the ketone moiety, e.g. under mild hydrolysis conditions as described hereinafter in the Examples. This present synthetic strategy is most preferred where X is NOH or $NNR^6R^7$, whereby the substituents $R^6$ and $R^7$ are as above defined.

Scheme 6

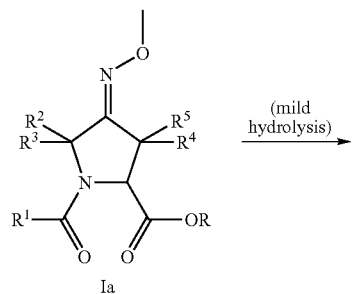

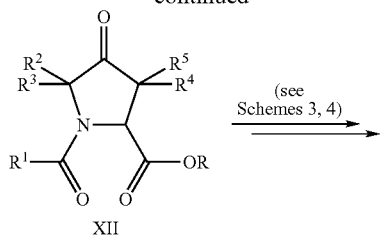

XII

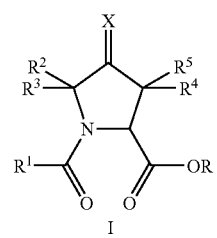

I

According to yet another process, pyrrolidine ester derivatives of general formula $(I)^X$ can be interconverted (transformed) to pyrrolidine ester derivatives of general formula $(I)^Y$ by a reaction sequence comprising saponification and re-esterification with alcohols $VI^Y$, using standard conditions well known to the person skilled in the art, as described hereinafter in the Examples and illustrated in Scheme 7.

Scheme 7

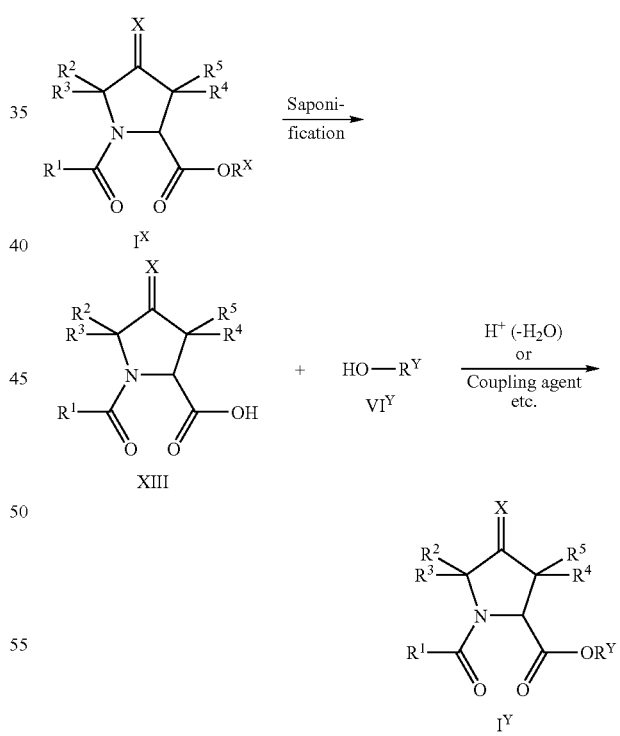

$R^x$ and $R^y$ are as above defined for R, but are different from each other for the purpose of the trans-esterification.

According to yet another process, pyrrolidine ester derivatives according to the general formula (I), whereby the substituents X, R and $R^{1-5}$ are as above defined, are prepared from the corresponding suitably N-protected 4-substituted pyrrolidine carboxylic acid derivatives V, whereby the substituent X is above defined, by a solid-phase protocol such as described in the examples and shown in Scheme 8, below. The N-Boc-protected 4-substituted pyrrolidine derivative V is reacted with a resin carrying a linker prone to cleavage by nucelophiles, e.g. with Kaiser oxime resin, using standard carbodiimide-mediated coupling conditions well known to the practitioner skilled in the art. Boc-deprotection with dilute TFA in DCM, or with $BF_3 \cdot OEt_2$ in dilute HOAc in DCM, affords compounds of formula XVI. The latter compound can be treated with acylating agents of general formula (IV), whereby the substituent $R^1$ is as above defined, and Y could be an appropriate leaving group. Preferred acylating agents IV are acid chlorides (IVa), used in conjunction with a tertiary amine base, or carboxylic acids (IVb), used in conjunction with a peptide coupling agent, such as e.g. DIC, EDC, TBTU, DECP, or others, to yield products of general formula XVII.

In order to obtain the final compounds of general formula (I), the linkage to the resin is cleaved by prolonged treatment with alcohols VI, and a tertiary, non-nucleophilic amine base, such as TEA, DIEA, DBU, or others. The circles in Scheme 8 symbolize the resin beads to which the corresponding compounds are linked during the solid phase synthesis. Other derivatives of formula (I) are prepared using known modifications to, or variations of, the Scheme 8 reaction sequence. Further to the above mentioned Kaiser oxime resin, other suitable reagents, notably resins, known to a person skilled in the art, could be employed for the solid-phase synthesis of compounds of general formula (I).

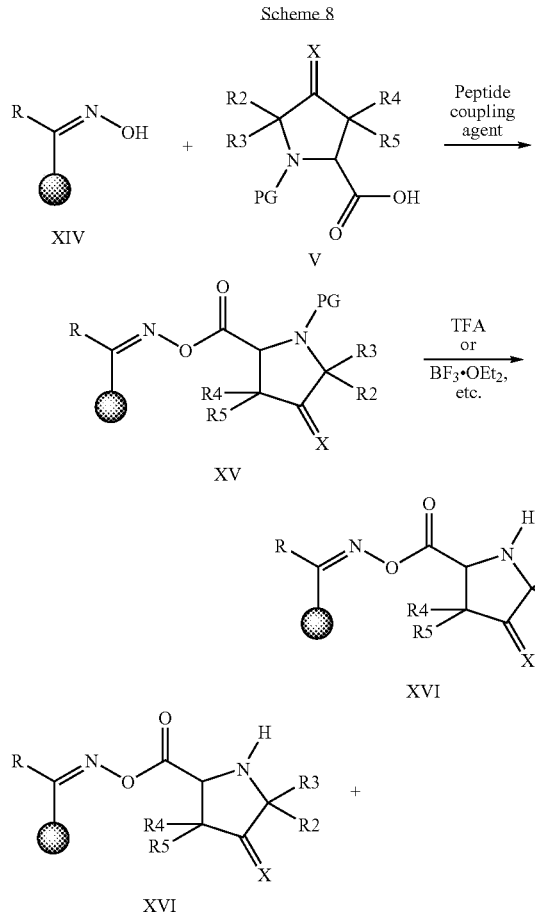

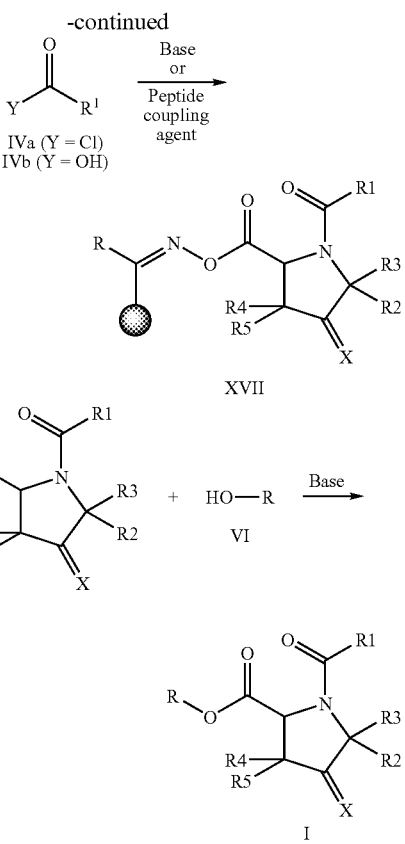

The reaction sequences outlined in the above Schemes provide enantiomerically pure compounds of formula (I), if enantiomerically pure starting materials are used. (R)- as well as (S)-enantiomers can be obtained depending upon whether (R)- or (S)-forms of commercially available compounds of formulas IV, V, X, and/or VI were used as the starting materials.

However, the reaction sequences outlined in the above Schemes usually provides mixtures of (E)- and (Z)-isomers with respect to the substituents on the exocyclic double bond of the pyrrolidine ring. In all cases studied, these (E)/(Z)-isomers could be separated by standard chromatography techniques well known to the person skilled in the art, such as by reversed phase high-pressure liquid chromatography (HPLC) or silica gel flash chromatography (FC). The assignment of the absolute configuration of the exocyclic double bond was performed using NMR-techniques well described in the literature as will be known to the practitioner skilled in the art (for configurationnal assignments of e.g. oxime functionalities, see e.g. E. Breitmaier, W. Voelter Carbon-13 NMR Spectroscopy, 3rd Ed, VCH, 1987, p. 240).

According to a further general process, compounds of formula (I) can be converted to alternative compounds of formula (I), employing suitable interconversion techniques such as hereinafter described in the Examples.

If the above set out general synthetic methods are not applicable for obtaining compounds according to formula (I) and/or necessary intermediates for the synthesis of compounds of formula (I), suitable methods of preparation known by a person skilled on the art should be used. In general, the synthesis pathways for any individual compound of formula (I) will depend on the specific substitutents of each molecule and upon the ready availability of intermediates necessary; again such factors being appreciated by those of ordinary skill in the art. For all the protection, de-protection methods, see Philip J. Kocienski, in *"Protecting Groups"*, Georg Thieme Verlag Stuttgart, New York 1994 and, Theodora W. Greene and Peter G. M. Wuts in *"Protective Groups in Organic Synthesis"*, Wiley-Interscience, 1991.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I) with a suitable base. Both types of salt may be formed or interconverted using ion-exchange resin techniques.

If the above set out general synthetic methods are not applicable for the obtention of compounds of formula (I), suitable methods of preparation known by a person skilled in the art should be used.

When employed as pharmaceuticals, the pyrrolidine derivatives of the present invention are typically administered in the form of a pharmaceutical composition. Hence, pharmaceutical compositions comprising a compound of formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides the compounds of formula (I) for use as antagonists of the oxytocin receptor, for the treatment or prevention of disorders mediated by the oxytocin receptor in mammals, notably of humans, either alone or in combination with other medicaments, e.g. in combination with a further OT antagonist.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the pyrrolidine derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyrrolidine compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the pyrrolidine derivatives of formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences,* 17th Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences.*

In the following the present invention shall be illustrated by means of some examples which are not construed to be viewed as limiting the scope of the invention. The HPLC, NMR and MS data provided in the examples described below were obtained as followed. The following abbreviations are hereinafter used in the accompanying examples: min (minute), hr (hour), g (gram), mmol (millimole), m.p. (melting point), eq (equivalents), mL (milliliter), µL (microliters), mL (milliliters), ACN (Acetonitrile), DBU (Diazabicyclo [5.4.0]undec-7-ene), DIEA (Diisopropylethylamine), CDCl$_3$ (deuterated chloroform), cHex (Cyclo-hexanes), DCM (Dichloromethane), DECP (Diethylcyanophosphonate), DIC (Diisopropyl carbodiimide), DMAP (4-Dimethylaminopyridine) DMF (Dimethylformamide), DMSO (Dimethylsulfoxide), DMSO-$d_6$ (deuterated dimethylsulfoxide), EDC (1-(3-Dimethyl-amino-propyl)-3-ethylcarbodiimide), EtOAc (Ethyl acetate), $Et_2O$ (Diethyl ether), HOBt (1-Hydroxybenzotriazole), $K_2CO_3$ (potassium carbonate), NaH (Sodium hydride), $NaHCO_3$ (Sodium bicarbonate), nBuLi (n Butyllithium), TBTU (O-Benzotriazolyl-N,N,N',N'-tetramethyluronium-tetrafluoroborate), TEA (Triethylamine), TFA (Trifluoro-acetic acid), THF (Tetrahydrofuran), $MgSO_4$ (Magnesium sulfate), PetEther (Petroleum ether), rt (room temperature).

EXAMPLES

Intermediate 1: (2S)-1-(tert-butoxycarbonyl)-4-oxo-2-pyrrolidinecarboxylic acid

Commercial (2S,4R)-1-(tert-butoxycarbonyl)-4-hydroxy-2-pyrrolidinecarboxylic acid (30 g, 0.13 mol) was dissolved in acetone (1500 ml). A mechanical stirrer was placed in the flask and the solution stirred vigorously. A freshly made solution of 8N chromic acid was prepared by dissolving chromium trioxide (66.7 g, 0.667 mol) in water (40 ml), adding concentrated sulphuric acid (53.3 ml) and adding enough water to bring the solution volume to 115 ml. The 8N chromic acid solution (115 ml) was then added dropwise over a period of 30 minutes with continued vigorous stirring, the reaction's exotherm being maintained at the optimal temperature of 25° C. by the use of an ice bath. After the complete addition of the chromic acid, the reaction mixture was stirred for a further 15 minutes—maintaining the optimal temperature of 25° C. The reaction mixture was then quenched by the addition of methanol (20 ml). Exotherm controlled by the use of an ice bath and, if necessary, direct addition of a small amount of crushed ice to the reaction mixture itself. The reaction mixture was filtered through a Celite pad and then concentrated in vacuo. The resulting acidic solution was then extracted with ethyl acetate (3×300 ml) and the combined organic layers washed with brine (2×100 ml). Organics then dried with magnesium sulfate and concentrated in vacuo. Crude product recrystallised from ethyl acetate to give the white crystalline product, (2S)-1-(tert-butoxycarbonyl)-4-oxo-2-pyrrolidinecarboxylic acid (22.55 g, 76%). The antipodal intermediate, (2R)-1-(tert-butoxycarbonyl)-4-oxo-2-pyrrolidinecarboxylic acid, was made according to the same protocol, starting from commercial (2R,4S)-1-(tert-butoxycarbonyl)-4-hydroxy-2-pyrrolidinecarboxylic acid.

1H NMR (360 MHz, CDCl3): 1.4 (m, 9H), 2.5–3.0 (m, 2H), 3.7–3.9 (m, 2H), 4.74 (dd, 1H)

Intermediate 2: 1-tert-butyl 2-methyl (2S-4-oxo-1,2-pyrrolidinedicarboxylate

A solution of (2S)-1-(tert-butoxycarbonyl)-4-oxo-2-pyrrolidinecarboxylic acid (1 g, 4.3 mmol) in a 1:1 mixture of methanol and toluene (60 ml) was made. Trimethylsilyl diazomethane (6.5 ml of a 2M solution in hexanes, 13 mmol) was then added dropwise to the stirred solution at room temperature under nitrogen. After completion of the evolution of nitrogen gas, the resulting yellow solution was evaporated in vacuo, and the residue filtered through a pad of silica gel, eluting with ethyl acetate. Removal of solvent from the filtrate gave a yellow oil (1.05 g, near quantitative yield).

$^1$H NMR (400 MHz, $CDCl_3$): 1.4 (m, 9H), 2.5 (m, 1H), 2.8–2.9 (m, 1H) 3.7 ( 2H), 4.6–4.8 (m, 1H).

Intermediate 3: 1-tert-butyl 2-methyl (2S,4EZ)-4-(chloromethylene)-1,2-pyrrolidinedicarboxylate Chloromethyltriphenylphosphonium iodide (270 mg, 0.62 mmol) was added to a solution of potassium tert-butoxide (67 mg, 0.59 mmol) in anhydrous diethyl ether (5 ml) under nitrogen and the resulting bright yellow mixture stirred for 30 minutes at ambient temperature. The reaction was then cooled to 0° C. and a solution of 1-tert-butyl 2-methyl (2S)-4-oxo-1,2-pyrrolidinedicarboxylate (100 mg, 0.41 mmol in 2 ml anhydrous diethyl-ether) was added dropwise. The reaction was then warmed to room temperature and stirred for 30 minutes before adding saturated aqueous ammonium chloride solution (0.5 ml). The organic layer was removed in vacuo, and the aqueous washed with diethyl ether (3×5 ml). The combined organic layers were dried with brine and magnesium sulfate before filtering and removal of solvent. The desired product was isolated by silica gel chromatography, eluting with 15% ethyl acetate in hexanes to give 105 mg (93% yield) as a off-white wax.

$^1$H NMR (400 MHz, $CDCl_3$): 1.4 (9H, m), 2.6–2.75 (m, 1H), 2.8–3.0 (m, 1H), 3.65 (s, 3H), 4.1 (m, 2H), 4.4–4.5 (m, 1H) 5.9–6.0 (m, 1H).

Intermediate 4: 1-tert-butyl 2-methyl (2S)-4-methylene-1,2-pyrrolidinedicarboxylate Methyltriphenylphosphonium bromide (22 g, 61.6 mmol) was added to a solution of potassium tert-butoxide (6.5 g, 57.6 mmol) in anhydrous diethyl ether (450 ml) at 0° C. under nitrogen and the resulting bright yellow mixture stirred for 30 minutes. A solution of 1-tert-butyl 2-methyl (2S)-4-oxo-1,2-pyrrolidinedicarboxylate (10 g, 41.1 mmol in 150 ml anhydrous diethyl ether) was added slowly to the reaction mixture, which was then warmed at 35° C. for 3 h. Saturated aqueous ammonium chloride solution (0.5 ml) was then added. The organic layer was removed, and the aqueous washed with diethyl ether (3×5 ml). The combined organic layers were dried with brine and magnesium sulfate before filtering and removal of solvent. Silica gel chromatography, eluting with 15% ethyl acetate in hexanes gave the desired product 6.9 g (70% yield) as a off-white wax.

$^1$H NMR (400 MHz, $CDCl_3$): 1.4 (9H, m), 2.5 (m, 1H), 2.8 (m, 1H), 3.65 (s, 3H), 4.0 (m, 2H), 4.3–4.5 (m, 1H), 4.9 (m, 2H).

Intermediate 5: 1-tert-butyl 2-methyl (2S,4EZ)-4-(cyanomethylene)-1,2-pyrrolidinedicarboxylate Diethyl cyanomethyl phosphonate (0.86 ml, 4.4 mmol) was dissolved in dry THF (50 ml) and the solution cooled to 0° C. Sodium hydride (205 mg of a 60% suspension in parrafin oil, 5.1 mmol) was then added cautiously and the reaction stirred for 30 min. The reaction mixture was then cooled to −78° C. and a solution of 1-tert-butyl 2-methyl (2S)-4-oxo-1,2-pyrrolidinedicarboxylate (1.0 g, 4.1 mmol) in dry THF (5 ml) was added dropwise. The reaction was then allowed to reach room temperature. Saturated aqueous ammonium chloride solution (15 ml) was then added, followed by ethyl acetate (100 ml). (The organic layer was removed, and the aqueous washed with ethyl acetate (3×5 ml). The combined organic layers were dried with brine and magnesium sulfate before filtering and removal of solvent. Silica gel chromatography, eluting with 35% ethyl acetate in hexanes gave the desired compound (860 mg, 80%) as an off-white wax.

¹H NMR (360 MHz, CDCl₃): 1.4 (m, 9H), 2.7–3.0 (m, 1H), 3.1–3.3 (m, 1H), 3.7 (m, 3H), 4.2–4.4 (m, 2H), 4.5–4.7 (m, 1H), 5.4 (m, 1H).

Intermediate 6: 1-tert-butyl 2-methyl (2S,4EZ)-4-benzylidene-1,2-pyrrolidinedicarboxylate Potassium-tert-butoxide (6.1 g, 54 mmol) was added portionwise to a solution of benzyltriphenylphosphonium chloride (22.45 g, 58 mmol) in anhydrous dichloromethane (400 ml) and the reaction stirred at ambient temperature for 1 h. The solution was then cooled to 0° C. and a solution of 1-tert-butyl 2-methyl (2S)-4-oxo-1,2-pyrrolidinedicarboxylate (9.36 g, 38.5 mmol) in dry dichloromethane (30 ml) was added dropwise. After stirring for a further 1 h at 0° C. the reaction was stirred for a further 3 h at ambient temperature. Saturated aqueous ammonium chloride solution (30 ml) was then added. The organic layer was removed, and the aqueous washed with dichloromethane (3×20 ml). The combined organic layers were dried with brine and magnesium sulfate before filtering and removal of solvent. Silica gel chromatography, eluting with 30% ether in hexanes gave the desired product 8.65 g (71% yield) as a pale yellow wax.

¹H NMR (400 MHz, CDCl₃): 1.5 (m, 9H), 2.8–3.0 (m, 1H), 3.2 (m, 1H), 3.7 (m, 3H), 4.2–4.4 (m, 2H), 4.5–4.6 (m, 1H), 6.3–6.4 (m, 1H), 7.1–7.5 (m, 5H).

Intermediate 7: (2S,4EZ)-1-(tert-butoxycarbonyl-4-(methoxyimino)-2-Pyrrolidinecarboxylic acid A solution was made containing (2S)-1-(tert-butoxycarbonyl)-4-oxo-2-pyrrolidinecarboxylic acid (5.0 g, 21 mmol) and O-methylhydroxylamine hydrochloride (2.7 g, 32.8 mmol) in chloroform (100 ml) containing triethyl-amine (5.5 g, 55 mmol). The reaction mixture was then stirred at ambient temperature over-night, prior to removal of solvent. The resultant crude reaction mixture was dissolved in ethyl acetate (150 ml) and washed rapidly with 1N HCl (40 ml). The acidic layer was then extracted with ethyl acetate (3×20 ml) and the combined organic layers washed with brine before drying over magnesiom sulfate, filtering and removal of solvent in vacuo. The desired product (5.3 g, 94%) was isolated as a pale yellow oil.

¹H NMR (400 MHz, CDCl₃): 1.45 (m, 9H), 2.8–3.2 (m, 2H), 3.9 (s, 3H), 4.2 (m, 2H), 4.5–4.7 (m, 1H).

Intermediate 8: (2 S,4EZ)-1-(tert-butoxycarbonyl-4-(ethoxyimino)-2-pyrrolidinecarboxylic acid A solution was made containing (2S)-1-(tert-butoxycarbonyl)-4-oxo-2-pyrrolidinecarboxylic acid (5.0 g, 22 mmol) and O-ethylhydroxylamine hydrochloride (6.4 g, 65.5 mmol) in a 1:1 mixture of pyridine and ethanol (100 ml). The reaction was heated to reflux for 2.5 h before cooling and removal of solvent. The residue was dissolved in ethyl acetate and washed rapidly with 1.3N HCl (40 ml). The acidic layer was then extracted with ethyl acetate (3×20 ml) and the combined organic layers washed with brine before drying over magnesiom sulfate, filtering and removal of solvent in vacuo. The desired product (5.5 g, 93%) was isolated as a pale yellow oil.

¹HNMR (400 MHz, DMSO): 1.3 (t, 3H), 1.55 (m, 9H), 2.9–2.7 (m, 1H), 3.4–3.1 (m, 1H), 4.1–4.3 (m, 4H), 4.6 (m, 1H), 12–13.5 (br, 1H).

Intermediate 9: (2S,4EZ)-4-[(allyloxy)imino]-1-(tert-butoxycarbonyl)-2-pyrrolidinecarboxylic acid A solution was made containing (2S)-1-(tert-butoxycarbonyl)-4-oxo-2-pyrrolidinecarboxylic acid (5.0 g, 22 mmol) and O-allylhydroxylamine hydrochloride monohydrate (7.2 g, 65.5 mmol) in a 1:1 mixture of pyridine and ethanol (100 ml). The reaction was heated to reflux for 2.5 h before cooling and removal of solvent. The residue was dissolved in ethyl acetate and washed rapidly with 1.3N HCl (40 ml). The acidic layer was then extracted with ethyl acetate (3×20 ml) and the combined organic layers washed with brine before drying over magnesium sulfate, filtering and removal of solvent in vacuo. The desired product (5.9 g, 94%) was isolated as a pale yellow oil.

¹H NMR (400 MHz, CDCl₃): 1.5 (m, 9H), 2.8–3.2 (m, 2H), 4.2 (m, 2H), 4.5–4.7 (m, 3H), 5.25 (m, 2H), 5.9 (m, 1H), 11.1 (broad S, 1H).

Intermediate 10: 1-[(aminooxy)methyl]-4-methoxybenzene

A solution was made of Boc hydroxylamine (2.0 g, 17.1 mmol) in dry THF (60 ml). Sodium hydride (1.1 g of a 60% suspension in paraffin oil, 25.7 mmol) was then added and the suspension stirred. A catalytic amount of KI was then added to the reaction prior to the cautious addition of 4-methoxybenzyl chloride (3.2 g, 20.4 mmol). The reaction was then allowed to stir overnight before removal of solvent in vacuo. The residue was taken up with diethyl ether (100 ml) and HCl gas bubbled in for 20 minutes, causing the start of precipitation of the product. The flask was stoppered and left to stand overnight. The product was then filtered off as a off-white wax (39–52% yield according to varying batches).

¹H NMR (400 MHz, D₂O): 3.8 (s, 3H), 5 (s, 2H), 7.0 (d, 2H), 7.4 (d, 2H).

Intermediate 11: (2S,4EZ)-1-(tert-butoxycarbonyl-4-{[(4-methoxybenzyl)oxy]imino}-2-pyrrolidine-carboxylic acid The same method as employed in the preparation of Intermediate 7, but starting from (2S)-1-(tert-butoxycarbonyl)-4-oxo-2-pyrrolidinecarboxylic acid (Intermediate 1) and 1[(aminooxy)methyl]-4-methoxy-benzene (Intermediate 10) gave the title compound as a gum in a 85% yield.

¹H NMR (400 MHz, DMSO): 1.5 (m, 9H), 2.7–2.9 (m, 1H) 3.9 (s, 3H), 4.2 (m, 3H), 4.6 (m, 1H), 5.15 (s, 2H), 7.1 (d, 2H), 7.45 (d, 2H).

Intermediate: 12: 2'-methyl[1,1'-biphenyl]-4-carboxylic acid

To a mixture of 4-bromobenzoic acid (30 g, 0.15 mol), 2-methylphenylboronic acid (24 g, 0.15 mol), sodium carbonate (250 g) in toluene (500 mL) and water (500 mL) was added tetrakis-triphenylphosphine palladium(0) (9 g, 0.0074 mol) under nitrogen atmosphere. The reaction mixture was refluxed for 10 h. After this time, 100 ml of 10% NaOH were added to the reaction mixture, the aqueous layer was separated and washed with toluene (2×200 mL). Acidification of the aqueous layer with 3N HCl solution gave a solid product, which was filtered, washed with water and dried. The crude product was then crystallised from toluene to yield 2'-methyl [1,1'-biphenyl]-4-carboxylic acid (20 g, 62.5%).

Conversely, the product could also be obtained from 1-bromo-2-methylbenzene and 4-carboxybenzeneboronic acid, using analogous conditions.

$^1$H NMR (300 MHz, DMSO): 2.2 (s, 3H), 7.2–7.4 (m, 4H), 7.43 (d, J=9 Hz, 2H), 7.99 (d, J=9 Hz, 2H), 13 (b, 1H).

Similarly, using the appropriate commercial boronic acids and arylbromides, the following, related intermediate 1,1'-biphenyl derivatives (12) were obtained: 4'-methyl[1,1'-biphenyl]-4-carboxylic acid; 2',3-dimethyl[1,1'-biphenyl]-4-carboxylic acid; 2',6'-dimethyl[1,1'-biphenyl]-4-carboxylic acid; 2-methyl[1,1'-biphenyl]4-carboxylic acid; 3-methyl[1,1'-biphenyl]-4-carboxylic acid; 2,2'-dimethyl[1,1'-biphenyl]-4-carboxylic acid; 2'-methoxy-[1,1'-biphenyl]-4-carboxylic acid; 3'-methoxy[1,1'-biphenyl]-4-carboxylic acid; 4'-methoxy[1,1'-biphenyl]4-carboxylic acid; 2'-chloro[1,1'-biphenyl]4-carboxylic acid; 3'-chloro[1,1'-biphenyl]-4-carboxylic acid; 4'-chloro[1,1'-biphenyl]4-carboxylic acid; 3',4'-dichloro[1,1'-biphenyl]4-carboxylic acid; 2'-(trifluoromethyl)[1,1'-biphenyl]-4-carboxylic acid; 3'-(trifluoromethyl)[1,1'-biphenyl]-4-carboxylic acid; 2'-cyano[1,1'-biphenyl]-4-carboxylic acid; 2',4'-difluoro[1,1'-biphenyl]4-carboxylic acid; 4-(2-pyridinyl)benzoic acid; 4-(3-pyridinyl)benzoic acid; 4-(4-pyridinyl)benzoic acid; 4-(5-pyrimidinyl)benzoic acid; and others.

Intermediate 13: 4-(3-methyl-2-pyridinyl)benzoic acid

A mixture of 2-bromo-3-methylpyridine (22.5 g, 0.1312 mol), 4(hydroxymethyl)phenylboronic acid (25 g, 0.164 mol), Pd(PPh$_3$)$_4$ (9.5 g, 0.0082 mol), and sodium carbonate (200 g in 500 ml of water) in toluene (750 ml) were refluxed under nitrogen atmosphere for 15 h. Separated the toluene layer and distilled under reduced pressure to give a residue. The residue was then purified by column chromatography to yield [4-(3-methyl-2-pyridinyl)phenyl]methanol (12 g, 47%).

To a solution of [4-(3-methyl-2-pyridinyl)phenyl]methanol (12 g, 0.06 mol) in dry DMF (150 mL) was added pyridiniumdichromate (91 g, 0.24 mol) and stirred at RT for 3 days. The reaction mixture was poured into water and extracted with ethyl acetate (250 mL). The organic layer was washed with water, brine, dried and concentrated. The crude was purified by column chromatography over silica gel to give 4-(3-methyl-2-pyridinyl)benzoic acid (3 g, 25%) as white solid.

$^1$H NMR (300 MHz, DMSO): 2.3 (s, 3H), 7.33 (dd, J=7.5 Hz, 5 Hz, 1H), 7.67 (d, J=8 Hz, 2H), 7.75 (d, J=7.5 Hz, 1H), 8.01 (d, J=8 Hz, 2H), 8.50 (d, J=5 Hz, 1H), 13 (b, 1H).

Intermediate 14: 4-(1-oxido-3-pyridinyl)benzoic acid

To a mixture of 4-tolylboronic acid (38 g, 0.28 mol), 3-bromopyridine (44 g, 0.28 mol), Na$_2$CO$_3$ (200 g) in toluene (500 ml) and water (500 ml) was added Pd(PPh$_3$)$_4$ (16 g, 0.014 mol), and refluxed for 16 h. The reaction mixture was cooled, and the separated organic layer was washed with water and brine, and dried. The solvent was removed to give 4-(3-pyridyl)toluene (42 g, 90%).

To a mixture of 4-(3-pyridyl)toluene (35 g, 0.207 mol) in pyridine (400 ml) and water (400 ml) was added KMnO$_4$ (163 g, 1.03 mol) in portions and refluxed for 12 h. The reaction mixture was filtered through celite and acidified with conc. HCl. The product was washed with water and dried to give 4-(3-pyridyl)benzoic acid (32 g, 76%) as a white solid. To a mixture of 4-(3-pyridyl)benzoic acid (22 g, 0.11 mol) in THF (2.51), mCPBA (152 g, 0.44 mol, 50%) was added and stirred at RT for 12 h. The solid was filtered, and washed with THF to give 4-(1-oxido-3-pyridinyl)benzoic acid (20 g, 86%).

$^1$H NMR (300 MHz, DMSO): 7.5–7.8 (m, 5H), 7.9 (d, J=8 Hz, 2H), 8.33 (d, J=5 Hz, 2H).

Similarly, starting from 4-tolylboronic acid (45 g, 0.33 mol) and 2-bromopyridine (52 g, 0.33 mol), the related intermediate 4-(1-oxido-2-pyridinyl)benzoic acid was obtained.

Example 1

General Procedure for the Saponification of methylesters of oximether- and/or olefin-type 2-pyrrolidinecarboxylic acid intermediates (Schemes 3, 7):

A solution of sodium hydroxide (73 mg, 1.81 mmol) in water (1.2 ml) was added to a proline oximether methyl ester derivative, e.g. methyl (2S,4 EZ)-4-(methoxyimino)-1-[(2'-methyl[1,1'-biphenyl]-4-yl)carbonyl]-2-pyrrolidinecarboxylate (391 mg, 1.1 mmol) in 3:1 dioxane:water (12 ml) and the reaction stirred for 3 h. The reaction mixture was then washed with diethyl ether (2×10 ml), and the aqueous phase acidified to pH 2 (0.1N HCl) and extracted into ethyl acetate. The ethyl acetate layer was then dried over magnesium sulfate, filtered and the solvent was then removed in vacuo to give the desired product, e.g. (2S,4EZ)-4-(methoxyimino)-1-[(2'-methyl[1,1'-biphenyl]-4-yl)carbonyl]-2-pyrrolidinecarboxylic acid in 91% yield as an oil which was used without further purification.

$^1$H NMR (300 MHz, CDCl$_3$): 2.25 (m, 3H, ArCH$_3$), 2.96–3.35 (m, 2H), 3.84 (m, 3H), 4.37 (br s, 2H), 5.17 (m, 1H), 7.14–7.32 (m, 4H, H arom.), 7.34–7.44 (m, 2H, H arom.), 7.53–7.63 (m, 2H, H arom.). M$^+$(APCI$^+$): 353: M$^-$(APCI$^-$): 351.1.

Example 2

General Protocols for the Esterification of oximether- and/or olefin-type 2-pyrrolidinecarboxylic acid intermediates (Schemes 2, 5, 7)

a) Methylesters (e.g. 1-tert-butyl 2-methyl (2S,4EZ-4-(methoxyimino)-1,2-pyrrolidinedicarboxylate):

A solution of the oximether- and/or olefin-type 2-pyrrolidinecarboxylic acid intermediate, e.g. (2S,4EZ)-1-(tert-butoxycarbonyl)-4-(methoxyimino)-2-pyrrolidinecarboxylic acid (0.648 g, 2.5 mmol), in a 1:1 mixture of methanol and toluene (35 ml) was made. Trimethylsilyl diazomethane (3.8 ml of a 2M solution in hexanes, 7.5 mmol) was then added dropwise to the stirred solution at room temperature under nitrogen. After completion of the evolution of nitrogen gas, the resulting yellow solution was evaporated in vacuo, and the residue filtered through a pad of silica gel, eluting with ethyl acetate. Removal of solvent from the filtrate gave the methylester product, e.g. 1-tert-butyl 2-methyl(2S,4EZ)-4-(methoxyimino)-1,2-pyrrolidinedicarboxylate, as a yellow oil (0.646 g, 95% yield).

b) Other esters (e.g. sec-butyl (2S,4EZ)-4-(methoxyimino)-1-[(2'-methyl[1,1'-biphenyl]-4-yl)carbonyl]-2-pyrrolidinecarboxylate):

A solution was made containing the the oximether- and/or olefin-type 2-pyrrolidinecarboxylic acid intermediate, e.g.

(2S,4EZ)-4-(methoxyimino)-1-[(2'-methyl[1,1'-biphenyl]-4-yl)carbonyl]-2-pyrrolidinecarboxylic acid (50 mg, 0.14 mmol), an alcohol, e.g. isobutanol (0.012 ml, 0.128 mmol) and DMAP (6 mg, 0.05 mmol) in anhydrous DCM (5 ml). At 0° C., EDC (27 mg, 0.14 mmol) in DCM (2.5 mL) was added dropwise. The reaction mixture was stirred 2 h at 0° C. followed by 4 h at r.t. The reaction mixture was concentrated in vacuo and the residue was redissolved in EtOAc. The resulting solution was washed with HCl 0.1N, water, $NaHCO_3$ sat and brine and dried over magnesium sulfate. After filtration through a pad of silica and evaporation of the solvents, the desired product, e.g. (2S,4EZ)-4-(methoxyimino)-1-[(2'-methyl[1,1'-biphenyl]-4-yl)carbonyl]-2-pyrrolidinecarboxylic acid was isolated as a mixture of two isomers as an oil in 69% yield (96.2% purity by HPLC).

$^1$H NMR (300 MHz, $CDCl_3$): 0.7–1.0 (m, 3H), 1.02–1.34 (m, 3H), 1.38–1.72 (m, 2H), 2.24 (m, 3H, $ArCH_3$), 2.75–3.18 (m, 2H), 3.84 (m, 3H, $NOCH_3$), 4.12–4.48 (m, 2H), 4.54–5.18 (m, 2H), 7.13–7.29 (m, 4H), 7.31–7.62 (m, 4H). $M^+(APCI^+)$: 409.

Example 3

Cyclopentyl (2S,4EZ)-4-(methoxyimino-1-[(2'-methyl[1,1'-biphenyl]-4-yl)carbonyl]-2-pyrrolidinecarboxylate Following the general methods as outlined in Example 2, starting from (2S,4EZ)-4-(methoxyimino)-1-[(2'-methyl[1,1'-biphenyl]-4-yl)carbonyl]-2-pyrrolidinecarboxylic acid and cyclopentanol, the title compound was isolated, after flash-chromatography, as a mixture of two isomers as an oil in 57% yield (95.6% purity by HPLC).

$^1$H NMR (300 MHz, $CDCl_3$): 1.47–1.98 (m, 8H), 2.24 (m, 3H, $ArCH_3$), 2.73–3.14 (m, 2), 3.84 (m, 3H, $NOCH_3$), 4.11–4.46 (m, 2H), 4.61 (br s, 1H), 4.99–5.32 (m, 2H), 7.15–7.28 (m, 4H), 7.31–7.41 (m, 2H), 7.51–7.62 (m, 2H). $M^+(APCI^+)$: 421.

Example 4

General Protocol for the solution-phase Synthesis of oximether pyrrolidine derivatives of general formula (I) (Scheme 1): e.g. methyl (2S,4EZ)-4-(methoxyimino)-1-[(2'-methyl[(1,1'-biphenyl]-4-yl)carbonyl]-2-pyrrolidinecarboxylate: methyl (2S,4E)-4-(methoximino)-1-[(2'-methyl[1,1'-biphenyl]-4-yl)carbonyl]-2-pyrrolidinecarboxylate; methyl (2S,4Z)-4-(methoxyimino)-1-[(2'-methyl[1,1'-biphenyl]-4-yl)carbonyl]-2-pyrrolidinecarboxylate; methyl (2S,4EZ)-4-(methoxyimino)-1-[(2'-fluoro[1,1'-biphenyl]-4-yl)carbonyl]-2-pyrrolidinecarboxylate.

a) Protocol for the N-deprotection Step

Method A: A solution was made containing e.g. 1-tert-Butyl 2-methyl (2S,4EZ)-4-(methoxyimino)-1,2-pyrrolidinedicarboxylate (0.892 g, 3.28 mmol), in anhydrous DCM (28 ml). TFA (20%, 7 mL) was added dropwise. The mixture was stirred at r.t. for 20 min. Solvents were evaporated and the desired product, e.g. methyl (2S,4EZ)-4-(methoxyimino)-2-pyrrolidinecarboxylate (0.564 g, quant.) was isolated as a yellow oil and used without further purification.

Method B: A solution was made containing e.g. 1-tert-Butyl 2-methyl (2S,4EZ)-4-(methoxyimino)-1,2-pyrrolidinedicarboxylate (60 mg, 0.22 mmol), in anhydrous DCM (6 ml). At 0° C., HCl gas was bubbled slowly through the reaction and the deprotection was followed by TLC. After approximately 30 minutes, the DCM was evaporated. The product was concentrated in vacuo from DCM (2–3 times) to remove the HCl. The desired product, e.g. methyl (2S,4EZ)-4-(methoxyimino)-2-pyrrolidinecarboxylate (38 mg, quant.) was isolated as a yellow solid and used without further purification.

b) Protocol for the N-capping Step

Method A (e.g. methyl (2S,4EZ)-4-4-(methoxyimino-1-[(2'-methyl[1,1'-biphenyl]-4-yl)carbonyl]-2-pyrrolidinecarboxylate): A solution of methyl-(2S,4EZ)-4-(methoxyimino)-2-pyrrolidinecarboxylate (0.564 g, 3.28 mmol), 2'-methyl[1,1'-biphenyl]-4-carboxylic acid (0.765 g, 3.60 mmol) and 4-dimethylaminopyridine (0.880 g, 7.21 mmol) in a 7:3 mixture of DCM and DMF (30 ml) was made. EDC (0.691 mg, 3.60 mmol) was added slowly at 0° C. The reaction mixture was stirred overnight at r.t. It was washed with water (twice 20 ml), dried over $MgSO_4$, filtrated and evaporated in vacuo. The resulting crude product mixture, methyl (2S,4EZ)-4-(methoxyimino)-1-[(2'-methyl[1,1'-biphenyl]-4-yl)carbonyl]-2-pyrrolidinecarboxylate, was purified by flash chromatography, unsing cyclohexane/EtOAc 8:2 as eluent. After several further chromatographies, (E)- and (Z)-isomers could be separated: methyl (2S,4E)-4-(methoxyimino)-1-[(2'-methyl[1,1'-biphenyl]-4-yl)carbonyl]-2-pyrrolidinecarboxylate (261 mg, 22%) was isolated as a colorless powder in 98.3% purity by HPLC, and methyl (2S,4Z)-4-(methoxyimino)-1-[(2'-methyl[1,1'-biphenyl]-4-yl)carbonyl]-2-pyrrolidinecarboxylate (237 mg, 20%) was isolated as a colorless powder in 98.3% purity by HPLC.

Methyl (2S,4E)$_4$-(methoxyimino)-1-[(2'-methyl[1,1'-biphenyl]4-yl)carbonyl]-2-pyrrolidinecarboxylate: M.p. 38° C.; IR (neat) v 2952, 1743, 1640, 1405, 1206, 1177, 1045, 851 $cm^{-1}$; $^1$H NMR (300 MHz, $CDCl_3$): 2.27 (s, 3H, $ArCH_3$), 2.92–3.18 (m, 2H), 3.81 (m, 3H), 3.87 (m, 3H), 4.37 (m, 2H), 5.20 (m, 1H), 7.16–7.32 (m, 4H, H arom.), 7.35–7.42 (m, 2H, H arom.), 7.55–7.67 (m, 2H, H arom.). $M^+(APCI^+)$: 367.3. Analysis calculated for $C_{28}H_{29}N_3O_4$ 0.1 $H_2O$: C, 68.50; H, 6.08; N, 7.61. Found: C, 68.23; H, 6.16; N, 7.45.

Methyl (2S,4Z)-4-(methoxyimino)-1-[(2'-methyl[1,1'-biphenyl]-4-yl)carbonyl]-2-pyrrolidinecarboxylate: M.p. 40° C.; IR (neat) v 2937, 1742, 1640, 1405, 1207, 1177, 1045, 754 $cm^{-1}$; $^1$HNMR (300 MHz, $CDCl_3$): 2.27(s, 3H, $ArCH_3$), 2.92–3.18 (m, 2H), 3.81 (m, 3H), 3.87 (m, 3H), 4.37 (m, 2H), 5.20 (m, 1H), 7.16–7.32 (m, 4H, H arom.), 7.35–7.42 (m, 2H, H arom.), 7.55–7.67 (m, 2H, H arom.). $M^+(APCI^+)$: 367.3. Analysis calculated for $C_{28}H_{29}N_3O_4$: C, 68.84; H, 6.05; N, 7.65. Found: C, 68.46; H, 6.26; N, 7.35.

Method B (e.g. methyl (2S,4EZ)-4-(methoxyimino)-1-[(2'-fluoro[1,1'-biphenyl]-4-yl)carbonyl]-2-pyrrolidinecarboxylate): To a solution of 2'-fluoro[1,1'-biphenyl]-4-carboxylic acid (69 mg, 0.32 mmol.) in 9 ml THF, were added oxalyl chloride (0.09 mL, 0.99 mmol) and DMF (three drops) under ice cooling. The mixture was stirred for 2 h at rt. The solvent was removed affording the corresponding acyl chloride, 2'-fluoro[1,1'biphenyl]-4-carbonyl chloride. The latter was now dissolved in THF (7 mL) and added slowly on a 0° C. solution containing the free NH-compound from the previous step, e.g. methyl (2S,4EZ)-4-(methoxyimino)-2-pyrrolidinecarboxylate (38 mg, 0.22 mmol), and triethylamine (2eq, 0.44 mmol, 0.06 ml) in THF/DCM 1:1 mixture (12 ml). The reaction mixture was stirred overnight at r.t. Pol-trisamine was added (69 mg, 3.45 mmol/g) in order to scavenge excess of acyl chloride. The mixture was shaken 5 h, filtered and the resulting solution was washed with NH$_4$Cl 20%, brine, and dried over MgSO$_4$. After filtration and evaporation of the solvents, the resulting dark oil (3.26 g) was purified by SPE (SAX sorbent) using neat DCM as eluent. The desired product, e.g. methyl (2S,4EZ)-4-(methoxyimino)-1-[(2'-fluoro[1,1'-biphenyl]-4-yl)carbonyl]-2-pyrrolidinecarboxylate was obtained as a mixture of two isomers as a white foam in 34% yield (97.3% purity by HPLC).

Methyl (2S,4EZ)-4-(methoxyimino)-1-[(2'-fluoro[1,1'-biphenyl]-4-yl)carbonyl]-2-pyrrolidinecarboxylate: $^1$H NMR (300 MHz, CDCl$_3$): 2.80–3.20 (m, 2H), 3.70–3.85 (m, 6H), 4.07–4.40 (m, 2H), 3.55–3.82 (m, 1H), 3.90–4.44 (m, 2H), 5.20 (m, 1H), 7.13–7.25 (m, 2H), 7.30–7.46 (m, 2H), 7.61(m, 4H). M$^+$(APCI$^+$): 371.2 c) E/Z-isomerisation

The pure E-isomer was isomerized to a mixture of the E/Z-isomers by the following procedure: the E-isomer was dissolved in dioxane/water 3:1 mixture. NaOH (1.7 eq; 0.52 mL of NaOH 1.6N) was added and the resulting solution was stirred 2 h at r.t. The mixture was neutralysed with HCl 0.1 N and lyophilised. The components of the resulting E/Z-mixture were separated and purified by flash chromatography using same conditions as described above.

Example 5

Methyl (2S,4EZ)-1-[(4'-fluoro[1,1'-biphenyl]4-yl)carbonyl]-4-(methoxyimino)-2-pyrrolidinecarboxylate Following the general methods as outlined in Example 4, starting 1-tert-butyl 2-methyl (2S,4EZ)-4-(methoxyimino)-1,2-pyrrolidinedicarboxylate and 4'-fluoro[1,1'-biphenyl]-4-carboxylic acid, the title compound was isolated, after flash-chromatography, as a mixture of two isomers as an oil in 39% yield (97.6% purity by HPLC).

$^1$H NMR (300 MHz, CDCl$_3$): 2.72–3.20 (m, 2H), 3.74–3.87 (m, 6H), 4.10–4.42 (m, 2H), 5.20 (m, 1H), 7.12–7.18 (m, 2H), 7.53–7.61 (m, 6H). M$^+$(APCI$^+$): 371.2

Example 6

Methyl (2S,4EZ)-4-(methoxyimino)-1-[4-(5-pyrimidinyl)benzoyl]-2-pyrrolidinecarboxylate Following the general methods as outlined in Example 4, starting from 1-tert-butyl 2-methyl (2S,4EZ)-4-(methoxyimino)-1,2-pyrrolidinedicarboxylate and 4-(5-pyrimidinyl)benzoic acid, the title compound was obtained, after flash-chromatography, as a mixture of two isomers as an oil in 68% yield (93.0% purity by HPLC).

$^1$H NMR (300 MHz, CDCl$_3$): 2.64–3.20 (m, 2H), 3.74–3.87 (m, 6H), 4.16–4.64 (m, 2H), 5.18 (m, 1H), 7.64–7.73 (m, 4H), 8.97 (d, 2H), 9.26 (s, 1H). M$^+$(APCI$^+$): 355.3.

Example 7

Methyl (2S,4EZ)-1-([1,1'-biphenyl]-4-ylcarbonyl)-4-(methoxyimino)-2-pyrrolidinecarboxylate Following the general methods as outlined in Example 4, starting from 1-tert-butyl 2-methyl(2S,4EZ)-4-(methoxyimino)-1,2-pyrrolidinedicarboxylate and [1,1'-biphenyl]-4-carbonyl chloride, the title compound was isolated, after flash-chromatography, as a mixture of two isomers as an oil in 31% yield (99% purity by HPLC).

$^1$H NMR (300 MHz, CDCl$_3$): 2.88 (m, 1H), 3.07 (m, 1H), 3.80 (m, 6H), 4.20–4.45 (m, 2H), 4.65 (br s, 1H), 5.15 (m, 1H), 7.33–7.49 (m, 4H), 7.54–7.69 (m, 5H). M$^+$(APCI$^+$): 353.2.

Example 8

Methyl (2S,4EZ)-4-(methoxyimino)-1-[4-(2-pyridinyl)benzoyl]-2-pyrrolidinecarboxylate Following the general method as outlined in Example 4 (Method B), starting from 1-tert-butyl 2-methyl (2S,4EZ)-4-(methoxyimino)-1,2-pyrrolidinedicarboxylate and 4-(2-pyridinyl)benzoic acid, the title compound was obtained, after flash-chromatography (eluent cyclohexane/ethyl acetate 8:2), as a mixture of two isomers in 45% yield (95% purity by HPLC).

$^1$H NMR (300 MHz, CDCl$_3$): 2.90–3.20 (m, 2H), 3.70–3.85 (m, 6H), 4.26–4.35 (m, 2H), 5.15 (m, 1H), 7.26 (m, 2H), 7.30–7.76 (m, 4H), 8.10 (m, 2H), 8.73 (m, 1H). M

Example 9

Methyl (2S,4EZ)-4-(methoxyimino)-1-[4-(3-methyl-2-pyridinyl)benzoyl]-2-pyrrolidinecarboxylate Following the general method as outlined in Example 4 (Method B), starting from 1-tert-butyl 2-methyl (2S,4EZ)-4-(methoxyimino)-1,2-pyrrolidinedicarboxylate and 4-(3-methyl-2-pyridinyl)benzoic acid, the title compound was obtained, after flash-chromatography (eluent cyclohexane/ethyl acetate 8:2), as a mixture of two isomers in 50% yield (100% purity by HPLC).

$^1$H NMR (300 MHz, CDCl$_3$); 2.38 (s, 3H), 2.80–3.20 (m, 2H), 3.70–3.85 (m, 6H), 4.21–4.41 (m, 2H), 5.16 (m, 1H), 7.64 (m, 6H), 8.55 (m, 1H). M$^+$(APCI$^+$): 368.2.

Example 10

General Protocol for the Solution-phase Synthesis of Oxime or Hydrazone Pyrrolidine Derivatives of General Formula (I) (Scheme 6)

a) Protocol for the Hydrolysis of the Oximether Group.

The starting oximether compounds, (0.14 mmol), paraformaldehyde powder (95%, 1.41 mmol) and Amberlyst 15 (30 mg) were mixed in acetone containing 10% of water (2 mL). The reaction was stirred 4 h at 60° C. Insoluble materials were filtered off and washed with a small amount of acetone. The filtrate was concentrated and the residue was diluted with DCM (15 mL). The organic solution was washed with brine (10 mL), dried over Na$_2$SO$_4$, and concentrated. The desired 4-ketopyrroldidine product was isolated as a yellow oil and used without further purification (92%).

b) Protocol for the Formation of Oxime and/or Hydrazone Compounds

A solution was made containing the ketopyrrolidine derivative from the previous step (0.11 mmol) and hydroxylamine hydrochloride (0.17 mmol) in chloroform (1 ml) containing triethylamine (0.29 mmol), or hydrazine hydrate (4% in EtOH). The reaction mixtures were then stirred at ambient temperature for one day, prior to removal of solvent. The resultant crude reaction mixtures were purified by column chromatography using DCM/MeOH (25:1) to collect the desired oxime or hydrazone products, respectively.

Example 11

General Protocol for the Solid-phase Synthesis of Pyrrolidine Ester Derivatives of General Formula (I) (Scheme 8):

a) Loading Step

Kaiser oxime resin (16.5 g, loading 1.57 mmol/g) was added to a solution of the relevant pyrrolidine carboxylic acid building block (51.8 mmol) and diisopropylcarbodiimide (8.1 ml, 51.8 mmol) in dry dichloromethane (150 ml). The resulting suspension was shaken overnight before filtering at the pump and washing sequentially with DMF, DCM and finally diethyl ether before drying at room temperature in vacuo.

b) N-deprotection Step

The resin obtained in the loading step was shaken with a 20% solution of trifluoroacetic acid in dichloromethane (200 ml) for 30 minutes prior to filtering at the pump and washing sequentially with aliquots of DMF, DCM and finally diethyl ether before drying at room temperature in vacuo.

c) N-capping Step

The resin from the previous step was transferred into a 96-well filter-plate (approx. 50 mg of dry resin/well) and each well treated with an N-reactive derivatising agent, e.g. with either of the following solutions:
a) an acid chloride (0.165 mmol) and diisopropylethylamine (0.165 mmol) in dry dichloromethane (1 ml), overnight
b) an acid (0.165 mmol) and DIC (0.165 mmol) in, depending on the solubility of the carboxylic acid, dry dichloromethane or NMP (1 ml) overnight.

The tubes were closed with a stopper and shaken overnight at ambient temperature. The resins were then filtered, washing the resin sequentially with aliquots of DMF, DCM and finally diethyl ether before drying at room temperature in vacuo.

d) Cleavage Step

A solution of MeOH (20 eq, 50 µL) and TEA (1 eq. 8 µL) in DCM (1.45 mL) was added to each tube containing the resin from the previous step. They were shaken for 2 days at room temperature. They were then filtered into individual vials and the solvent removed in a vacuum centrifuge to yield about 10 mg of the corresponding products (between 40 and 50% yield). The products were characterised by LC (MaxPlot detection between 230 and 400 nm) and mass spectrometry (ES+). All of the following examples were identified based on the observation of the correct molecular ion in the mass spectrum, and were shown to be at least 40% pure (usually 60–95% pure) by LC.

Example 12

Ethyl (2S,4EZ)-1-([1,1'-biphenyl]-4-ylcarbonyl)-4-(methoxyimino)-2-pyrrolidinecarboxylate Following the general method as outlined in Example 11, starting from (2S,4EZ)-1-(tert-butoxycarbonyl)-4-(methoxyimino)-2-pyrrolidinecarboxylic acid, [1,1'-biphenyl]-4-carbonyl chloride, and ethanol, the title compound was isolated as a mixture of two isomers in 87.2% purity by HPLC.

$^1$H NMR (300 MHz, CDCl$_3$): 1.43 (m, 314), 2.76–3.18 (m, 2H), 3.74–3.94 (m, 5H), 4.09–4.48 (m, 2H), 5.14 (m, 1H), 7.32–7.51 (m, 4H), 7.52–7.70 (m, 5H). M$^+$(APCI$^+$): 367.

Example 13

Methyl (2S,4EZ)-1-[(2'-chloro[1,1'-biphenyl]-4-yl)carbonyl]-4-(methoxyimino)-2-pyrrolidinecarboxylate Following the general method as outlined in Example 11, starting from (2S,4EZ)-1-(tert-butoxycarbonyl)-4-(methoxyimino)-2-pyrrolidinecarboxylic acid, 2'-chloro[1,1'-biphenyl]-4-carboxylic acid, and methanol, the title compound isolated as a mixture of two isomers in 92.3% purity by HPLC.

$^1$H NMR (300 MHz, CDCl$_3$): 2.85 (m, 1H), 3.05 (m, 1H), 3.72–3.94 (m, 6H), 4.27 (m, 1H), 4.41 (m, 1H), 4.68 (br s, 1H), 5.15 (m, 1H), 7.23–7.35 (m, 3H), 7.42–7.53 (m, 3H), 7.55–7.64 (m, 2H). M$^+$(APCI$^+$): 387.

Example 14

Methyl (2S,4EZ)-1-[(2'-cyano[1,1'-biphenyl]-4-yl)carbonyl]-4-(methoxyimino)-2-pyrrolidinecarboxylate Following the general method as outlined in Example 11, starting from (2S,4EZ)-1-(tert-butoxycarbonyl)-4-(methoxyimino)-2-pyrrolidinecarboxylic acid, 2'-cyano[1,1'-biphenyl]-4-carboxylic acid, and methanol, the title compound was isolated as a mixture of two isomers in 91.6% purity by HPLC.

$^1$H NMR (300 MHz, CDCl$_3$): 2.75–3.18 (m, 2H), 3.72–3.94 (m, 6H), 4.25 (m, 1H), 4.41 (m, 1H), 4.62 (br s, 1H), 5.15 (m, 1H), 7.40–7.55 (m, 3H),7.56–7.71 (m, 4H), 7.77 (m, 1H). M$^+$(APCI$^+$): 378.

Example 15

Methyl (2S,4EZ)-4-(methoxyimino)-1-{[2'-(trifluoromethyl)[1,1'-biphenyl]-4-yl]carbonyl}-2-pyrrolidinecarboxylate Following the general method as outlined in Example 11, starting from (2S,4EZ)-1-(tert-butoxycarbonyl)-4-(methoxyimino)-2-pyrrolidinecarboxylic acid, 2'-(trifluoromethyl)[1,1'-biphenyl]-4-carboxylic acid, and methanol, the title compound was isolated as a mixture of two isomers in 86.3% purity by HPLC.

$^1$H NMR (300 MHz, CDCl$_3$): 2.85 (m, 1H), 3.06 (m, 1H), 3.72–3.94 (m, 6H), 4.26 (m, 1H), 4.41 (m, 1H), 4.62 (br s, 1H), 5.17 (m, 1H), 7.29 (m, 1), 7.37 (m, 2H), 7.48 (m, 1H), 7.56 (m, 3H), 7.74 (m, 1H). M$^+$(APCI$^+$): 421.

Example 16

Methyl (2S,4EZ)-1-[(2'-methoxy[1,1'-biphenyl]-4-yl)carbonyl]-4-(methoxyimino)-2-pyrrolidinecarboxylate Following the general method as outlined in Example 11, starting from (2S,4EZ)-1-(tert-butoxycarbonyl)4-(methoxyimino)-2-pyrrolidinecarboxylic acid, 2'-methoxy[1,1'-biphenyl]-4-carboxylic-acid, and methanol, the title compound was isolated as a mixture of two isomers in 92.1% purity by HPLC.

¹H NMR (300 MHz, CDCl₃): 2.85 (m, 1H), 3.06 (m, 1H), 3.67–3.94 (m, 9H), 4.23–4.49 (m, 1H), 5.14 (m, 1H), 6.94–7.07 (m, 2H), 7.26–7.67 (m, 6H). M⁺(APCI⁺): 383.

Example 17

Methyl (2S,4EZ)-1-[(2',6'-dimethyl[1,1'-biphenyl]-4-yl)carbonyl]-4-(methoxyimino)-2-pyrrolidinecarboxylate Following the general method as outlined in Example 11, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and methanol, the title compound was isolated as a mixture of two isomers in 88.3% purity by HPLC.

¹H NMR (300 MHz, CDCl₃): 1.98 (s, 3H), 2.00 (s, 3H), 2.67–3.18 (m, 2H), 3.65–3.94 (m, 6H), 4.12–4.75 (m, 3H), 5.15 (m, 1H), 7.05–7.27 (m, 5H), 7.35–7.67 (m, 2H). M⁺(APCI): 381.

Example 18

Methyl (2S,4EZ)-1-[(2',3-dimethyl[1,1'-biphenyl]4-yl)carbonyl]-4-(methoxyimino)-2-pyrrolidinecarboxylate Following the general method as outlined in Example 11, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and methanol, the title compound was isolated as a mixture of two isomers in 81.4% purity by HPLC.

¹H NMR (300 MHz, CDCl₃): 2.20–2.45 (m, 6H), 2.72–3.20 (m, 2H), 3.65–3.94 (m, 6H), 3.96–4.24 (m, 2H), 5.11 (m, 1H), 7.10–7.29 (m, 7H). M⁺(APCI⁺): 381.

Example 19

Methyl (2S,4EZ)-1-[(3-methyl[1,1'-biphenyl]-4-yl)carbonyl]-4-(methoxyimino)-2-pyrrolidinecarboxylate Following the general method as outlined in Example 11, starting from (2S,4EZ)-1-(tert-butoxycarbonyl)-4-(methoxyimino)-2-pyrrolidinecarboxylic acid, 3-methyl[1,1'-biphenyl]-4-carboxylic acid, and methanol, the title compound isolated as a mixture of two isomers in 82.3% purity by HPLC.

¹H NMR (300 MHz, CDCl₃):2.40 (m, 3H, ArCH₃), 2.65–3.20 (m, 2H), 3.74–3.87 (m, 6H), 3.92–4.20 (m, 2H), 5.10 (m, 1H), 7.16–7.48 (m, 2H), 7.56 (m, 2H). M⁺(APCI⁺): 367.

Example 20

Methyl (2S,4EZ)-1-[(3',4'-dichloro[1,1'-biphenyl]-4-yl)carbonyl]-4-(methoxyimino)-2-pyrrolidinecarboxylate Following the general method as outlined in Example 11, starting from (2S,4EZ)-1-(tert-butoxycarbonyl)-4-(methoxyimino)-2-pyrrolidinecarboxylic acid, 3',4'-dichloro[1,1'-biphenyl]-4-carboxylic acid, and methanol, the title compound was isolated as a mixture of two isomers in 91.9% purity by HPLC.

¹H NMR (300 MHz, CDCl₃): 2.72–3.18 (m, 2H), 3.65–3.94 (m, 6H), 4.21 (m, 1H), 4.37 (m, 1H), 5.15 (m, 1H), 7.35–7.69 (m, 7H). M⁺(APCI⁺): 421.

Example 21

Preparation of a Pharmaceutical Formulation

The following formulation examples illustrate representative pharmaceutical compositions according to the present invention, being not restricted thereto.

Formulation 1—Tablets

A pyrrolidine compound of formula (I) is admixed as a dry powder with a dry gelatin binder in an approximate 1:2 weight ration. A minor amount of magnesium stearate is added as a lubricant. The mixture is formed into 240–270 mg tablets (80–90 mg of active pyrrolidine compound per tablet) in a tablet press.

Formulation 2—Capsules

A pyrrolidine compound of formula (I) is admixed as a dry powder with a starch diluent in an approximate 1:1 weight ratio. The mixture is filled into 250 mg capsules (125 mg of active pyrrolidine compound per capsule).

Formulation 3—Liquid

A pyrrolidine compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A pyrrolidine compound of formula (I) is admixed as a dry powder with a dry gelatin binder in an approximate 1:2 weight ratio. A minor amount of magnesium stearate is added as a lubricant. The mixture is formed into 450–900 mg tablets (150–300 mg of active pyrrolidine compound) in a tablet press.

Formulation 5—Injection

A pyrrolidine compound of formula (I) is dissolved in a buffered sterile saline injectable aqueous medium to a concentration of approximately 5 mg/ml.

Example 22

Biological Assays

The compounds according to formula (I) may be subjected to the following assays:

a) In Vitro Competition Binding Assay on hOT Receptor with Scintillation Proximity Assay (see Cook, N. D. et al. *Pharmaceutical Manufacturing International* 1992; p.49–53)

This assay allows to determine the affinity of the test compounds for the human Oxytocin (hOT) receptor. Membranes from HEK293EBNA (cells expressing the hOT receptor) were suspended in buffer containing 50 mM Tris-HCl, pH 7.4, 5 mM MgCl2 and 0.1% BSA (w/v). The membranes (2–4 µg) were mixed with 0.1 mg SPA bead coated with wheat-germ aglutinin (WGA-PVT-Polyethylene Imine beads from Amersham) and 0.2 nM of the radiolabelled [¹²⁵I]-OVTA (OVTA being Ornithin Vasoactive, an analogue of OT for competitive binding experiments). Nonspecific binding was determined in the presence of 1 μM Oxytocin. The total assay volume was 100 μl. The plates (Corning® NBS plate) were incubated at room temperature for 30 min and counted on a Mibrobeta® plate scintillation counter. Competitive binding was performed in presence of compounds of formula (I) at the following concentrations: 30 μM, 10 μM, 1 μM, 300 nM, 100 nM, 10 nM, 1 nM, 100 pM, 10 pM. The competitive binding data were analysed using the iterative, nonlinear, curve-fitting program, "Prism" (GraphPad Software, Inc).

The ability of the pyrrolidine derivatives of formula (I) to inhibit the binding of $^{125}$I-OVTA to the OT-receptor was assessed using the above described in vitro biological assay. Representative values for some example compounds are given in Table 1, where the binding affinity of the compounds is expressed by the $IC_{50}$ (μM) which is the concentration upon which 50% inhibition of OT-R is achieved. From these values, it can be derived that said test compounds according to formula (I) do show a significant binding to the oxytocin receptor.

According to a preferred embodiment, the compounds of the invention display binding affinities ($K_i$(μM)) of less 0.40 μM, more preferred of less than 0.1 μM.

TABLE 1

| Structure | IUPAC-Name | Binding affinity human OT-R $IC_{50}$ (μM) |
|---|---|---|
| 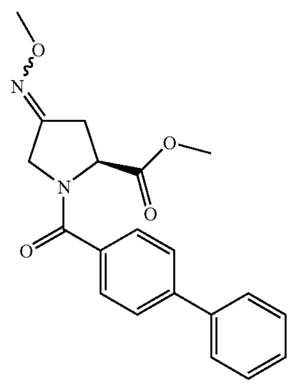 | Methyl (2S,4EZ)-1-([1,1'-biphenyl]-4-ylcarbonyl)-4-(methoxyimino)-2-pyrrolidinecarboxylate | 0.045 |
| 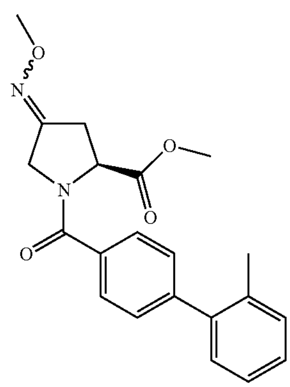 | Methyl (2S,4EZ)-4-(methoxyimino)-1-[(2'-methyl[1,1'-biphenyl]-4-yl)carbonyl]-2-pyrrolidinecarboxylate | 0.028 |
| 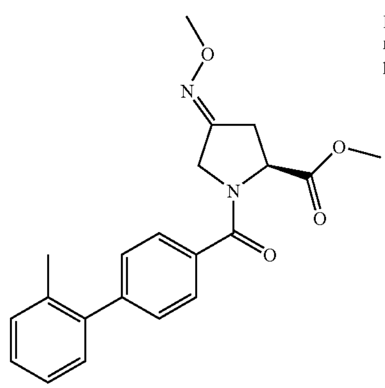 | Methyl (2S,4E)-4-(methoxyimino)-1-[(2'-methyl[1,1'-biphenyl]-4-yl)carbonyl]-2-pyrrolidinecarboxylate | 0.036 |

TABLE 1-continued

| Structure | IUPAC-Name | Binding affinity human OT-R IC$_{50}$ (µM) |
|---|---|---|
| 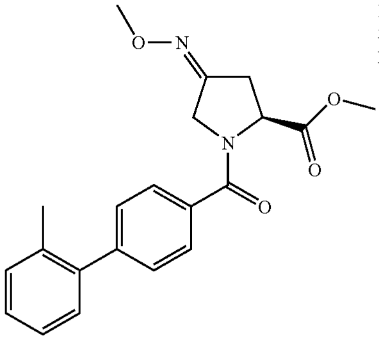 | Methyl (2S,4Z)-4-(methoxyimino)-1-[(2'-methyl[1,1'-biphenyl]-4-yl)carbonyl]-2-pyrrolidinecarboxylate | 0.012 |
| | Methyl (2S,4EZ)-4-(methoxyimino)-1-[(2'-fluoro[1,1'-biphenyl]-4-yl)carbonyl]-2-pyrrolidinecarboxylate | 0.10 | b) Functional Assay No. 1: Inhibition of Oxytocin Mediated Ca$^{2+}$-mobilization by FLIPR® (Fluorimetric Imaging Plate Reader)

The action of OT on the OT-receptor triggers a complex cascade of events in the cell which leads to an increase in the intra-cytoplasmic Ca$^{2+}$ concentration. This increase in Ca$^{2+}$ concentration results from both calcium release from the sarcoplasmic reticulum (calcium stores) into the cytoplasm and from calcium influx from the extracellular space through Ca$^{2+}$ channels. This Ca$^{2+}$ mobilization into the cytoplasm triggers the contractile machinery of the myometrial cells which leads to uterine contractions (see Gimpl G. and Fahrenholz, F. *Physiological Reviews* 2001, 81, 629–683 as well as Mitchell, B. F. and Schmid, B. J *Soc. Gynecol. Invest.* 2001, 8,122–33).

This assay allows the measurement of the inhibition of OT/OT-R mediated calcium mobilization by test compounds of formula (I).

FLIPR® is a fluorimetric imaging device using a laser (Argon-ion laser) for simultaneous illumination and reading (cooled CCD camera) of each well of a 96-well-plate, thus enabling rapid measurements on a large number of samples.

Preparing the plates: FLIPR-plates were pre-coated with PLL (Poly-L-Lysine) 10 µg/ml+0.1% gelatine to attach HEK293EBNA cells (Human Embryonic Kidney cells expressing the hOT receptor) and incubated for 30 min up to 2 days at 37° C. The cells were plated out into 96-well-plates (60000 cells/well).

Labelling with fluo-4: 50 µg of fluo-4 (Ca2+ sensitive fluorescent dye) were dissolved in 20 µl pluronic acid (20% in DMSO). The dissolved fluo-4 was then diluted in 10 ml DMEM (Dubecco's Minimal Essential Medium)-F12 culture medium. The plates were washed one time with DMEM-F12 medium. 100 µl of the fluo-4 containing-DMEM-F12 medium were added to the HEK-cells which were incubated for 1.5–2 h in this fluorescent medium. Fluo-4 is taken up by the cytoplasm of the cells.

Buffer: 145 mM NaCl, 5 mM KCl, 1 mM MgCl$_2$, 10 mM Hepes, 10 mM Glucose, EGTA (Ethylene-bis oxyethylene nitrilo tetraacetic acid). The pH was adjusted to 7.4.

Performance of the assay: A minimum of 80 µl/well of compounds of formula (I) (5×) in the above buffer (1×) were prepared (96-well-plates). The compounds of formula (I) were added to the 96-well-plates at different concentrations (30 µM, 10 µM, 1 µM, 300 nM, 100 nM, 10 nM, 1 nM, 100 pM, 10 pM). OT was added at a concentration of 40 nM.

The relative fluorescence of Fluo-4 ($\lambda_{ex}$=488 nm, $\lambda_{em}$=590 nm) is then measured by the FLIPR in presence or absence of compounds of formula (I). The fluorescence of the marker being sensitive to the amount of Ca$^{2+}$, the Ca$^{2+}$ movements can be detected. Then, the ability of compounds of formula (I) to antagonize the oxytocin-induced intracellular Ca$^{2+}$-mobilization mediated by the oxytocin receptor may be determined.

The activities of the pyrrolidine derivatives according to formula (I) were assessed using the above described in vitro biological assay. Representative values for some example compounds are given in Table 2. The values refer to the concentration of the test compounds according to formula (I) necessary to antagonize by 50% the OT/OTR intracellular Ca$^{2+}$-mobilization. From the values, it can be derived that said example compounds according to formula (I) do exhibit a significant activity as oxytocin receptor antagonists.

TABLE 2

| Structure | IUPAC-Name | Inhibition of Ca$^{2+}$ mobiliation, hOT-R IC$_{50}$ (μM) |
|---|---|---|
| 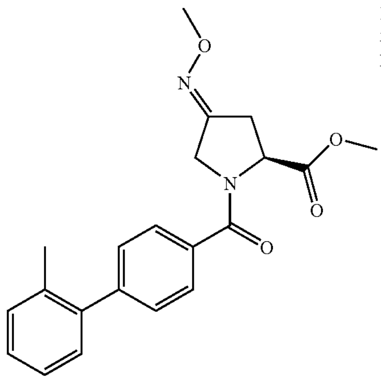 | Methyl (2S,4E)-4-(methoxyimino)-1-[(2'-methyl[1,1'-biphenyl]-4-yl)carbonyl]-2-pyrrolidinecarboxylate | 0.015 |
|  | Methyl (2S,4Z)-4-(methoxyimino)-1-[(2'-methyl[1,1'-biphenyl]-4-yl)carbonyl]-2-pyrrolidinecarboxylate | 0.015 | c) Functional Assay No. 2: Inhibition of IP3 (Inositol Tri-Phosphate)-Synthesis in HEK/EBNA-OTR cells The interaction of OT on the OT-receptor leads to the IP3 synthesis, IP3 being a second messenger for the Ca$^{2+}$ release from sarcoplasmic reticulum, involved in the uterine contraction triggering process (see Mitchell, B. F. and Schmid, B. *J. Soc. Gynecol. Invest.* 2001, 8,122–33).

This assay can be used to show the inhibition of the OT/OT-R mediated IP3 synthesis by using test compounds of formula (I).

Stimulation of the cells: HEK/EBNA OTR (rat or human) cells are plated out-into costar 12-well plates, and equilibrated for 15–24 h with 4 μCi/ml radiolabelled [$^3$H]-Inositol with 1% FCS (0.5 ml/well) and without inositol supplement. The medium containing the label is aspirated. DMEM medium (without FCS, inositol), 20 mM Hepes (4-(2-hydroxyethyl)-1-piperazine-ethane-sulphonic acid), 1 mg/ml BSA containing 10 mM LiCl (freshly prepared), are added and incubated for 10–15 min at 37° C. The agonist (i.e. oxytocin used at a concentration of 10 nM) and the antagonists (i.e. the tests compounds of formula (I) can be used in a concentration of 10 μM, 1 μM, 300 nM, 100 nM, 10 nM, 1 nM, 100 pM, 10 pM, 3 pM) can be added at the required time (15–45 min), followed by aspiration of the medium. In the presence of OT, the radiolabelled inositol is converted to radiolabelled IP3. Antagonizing OT at the OT-receptor inhibits the IP3 formation.

The amount of the radiolabelled IP3 may be determined through the ensuing work-up. The reaction is stopped with 1 ml STOP-solution (i.e. 0.4 M perchloric acid), and let sit for 5–10 min at Room Temperature. Then, 0.8 ml are transferred into tubes containing 0.4 ml of neutralizing solution (0.72 M KOH/0.6M KHCO$_3$), and the tubes vortexed and kept in the cold at least for 2 h.

Separation of IP's: The samples are spun in a table top centrifuge at 3000–4000 rpm for 15 min. 1 ml of the supernatant is transferred to new tubes containing 2.5 ml H$_2$O. Packed resin (Dowex AG1×8) is equilibrated with 20 ml H$_2$O, and the whole samples are poured onto the chromatography columns, thus separating the mixture. To remove free inositol, two washes with 10 ml H$_2$O are carried out.

Elution of total IP's: Elution is achieved using 3 ml 1M ammonium formate/0.1M formic acid. The eluant is collected in scintillation counting tubes, after the addition of 7 ml of scintillation liquid. The amount of [$^3$H]-IP3 is determined by a scintillating counter.

The ability of compounds of formula(I) to effectively antagonize oxytocin-induced IP3synthesis mediated by the oxytocin receptor, can be assessed using the above described in vitro biological assay.

TABLE 3

| Structure | IUPAC-Name | Inhibition of IP3-synthesis, ratOT-R IC$_{50}$ (μM) |
|---|---|---|
| 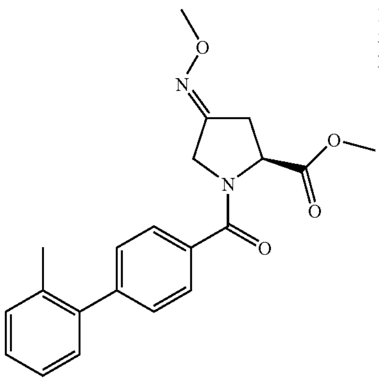 | Methyl (2S,4E)-4-(methoxyimino)-1-[(2'-methyl[1,1'-biphenyl]-4-yl)carbonyl]-2-pyrrolidinecarboxylate | 0.077 |
| | Methyl (2S,4Z)-4-(methoxyimino)-1-[(2'-methyl[1,1'-biphenyl]-4-yl)carbonyl]-2-pyrrolidinecarboxylate | 0.023 | d) In Vivo Model for Inhibtion of Uterine Contractions

The assay evaluates the biological effect of tested compounds in an in vivo model of preterm labor, premature birth.

Non-pregnant Charles River CD (SD) BR female rats (9–10 weeks old, 200–250 g) were treated at 18 and 24 hours before the experiment with 250 μg/kg, i.p. diethylstilbestrol (DES). For the assay, the animal was anaesthetised with urethane (1.75 g/kg, i.p.) and placed on a homeothermic operating table. The trachea was isolated and cannulated with a suitable polyethylene (PE) tubing. A midline incision at the hypogastrium level was made and one uterine horn exposed, its cephalic end cannulated with a PE240 tubing and, after filling the internal cavity with 0.2 ml of sterile physiological saline, connected to a "Gemini" amplifying/recording system via a P23ID Gould Statham pressure transducer.

One jugular vein was isolated, cannulated with a PE60 tubing and connected to a butterfly needle to provide an i.v. route of administration of the test compounds via a dispensing syringe.

In the case of intraduodenal administration of the test compounds, the duodenum can be isolated and similarly cannulated through a small incision in its wall.

One carotid artery was also isolated and cannulated with PE60 catheter and connected to a suitable syringe for blood sample collection.

After a stabilization period and throughout the experiment, the same dose of oxytocin was repeatedly injected intravenously at 30-min intervals. When reproducible contractile responses of the uterus to the same OT stimulus (selected dose of oxytocin) were obtained, the dose of the test compound or of the reference (vehicle) was administered. Further injection cycles of the same dose of oxytocin, were continued (OT injections at 30-min intervals) for a suitable time after treatment to assess the inhibitory effects and the reversibility of these effects.

The contractile response of the uterus to oxytocin was quantified by measuring the intrauterine pressure and the number of contractions. The effect of the reference and test compounds was evaluated by comparing pre- and post-treatment pressure values. In addition, at 2, 30, 90 and 210 minutes after test compound administration, a 0.5-ml blood sample was withdrawn from the cannulated carotid artery of each experimental animal. Plasma was obtained by standard laboratory procedure and the resulting samples were stored at −20° C.

The activities of the pyrrolidine derivatives of formula (I) may be assessed using the above described in vivo biological assay. Representative values for one example compound are given in Table 4. The values refer to the capacity of the example compound according to formula (I) to effectively antagonize oxytocin-induced uterine contractions in the rat. From the values shown in Table 4 it may be derived that said example test compound according to formula (I) does exhibit a significant activity as tocolytic, i.e. uterine-relaxing, agent.

TABLE 4

| Structure | IUPAC-Name | Route of administration/ Vehicle | % Reduction of Uterine Contraction | Dose (mg/kg) |
|---|---|---|---|---|
| 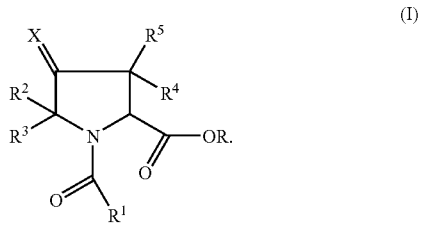 | Methyl (2S,4Z)-4-(methoxyimino)-1-[(2'-methyl[1,1'-biphenyl]-4-yl)carbonyl]-2-pyrrolidinecarboxylate | intravenous; PEG400/saline 50:50; 5 ml/kg infusion | −35.4 ± 7.0<br>−49.0 ± 6.5<br>−51.8 ± 9.2 | 1<br>3<br>10 |

The invention claimed is:

1. A pharmaceutical composition comprising a pyrrolidine ester according to formula (I), or a pharmaceutically acceptable salt thereof, (I)

as well as its geometrical isomers, its optically active forms as enantiomers, diastereomers and its racemate forms, as well as pharmaceutically acceptable salts thereof, wherein
X is selected from the group consisting of $CR^6R^7$, $NOR^6$, $NNR^6R^7$;
R is selected from the group consisting of $C_1$–$C_6$ alkyl, $C_2$–$C_6$ alkenyl, $C_2$–$C_6$ alkynyl, aryl, $C_1$–$C_6$-alkyl aryl, $C_1$–$C_6$-alkyl-saturated 3–8-membered cycloalkyl, and $C_1$–$C_6$-alkyl-unsaturated 3–8-membered cycloalkyl;
$R^1$ is selected from the group consisting of $C_1$–$C_6$-alkyl, aryl, saturated or unsaturated 3–8-membered cycloalkyl, acyl, and $C_1$–$C_6$-alkyl aryl, wherein said cycloalkyl or aryl groups may be fused with 1–2 further cycloalkyl groups or aryl groups;
$R^2$, $R^3$, $R^4$ and $R^5$ are independently from each other selected from the group consisting of hydrogen, halogen, $C_1$–$C_6$-alkyl;
$R^6$ and $R^7$ are independently selected from the group consisting of hydrogen, $C_1$–$C_6$ alkyl, $C_2$–$C_6$ alkenyl, $C_2$–$C_6$ alkynyl, $C_1$–$C_6$ alkoxy, $C_1$–$C_6$ thioalkoxy, halogen, cyano, nitro, acyl, alkoxycarbonyl, aminocarbonyl, aryl, $C_1$–$C_6$-alkyl aryl, $C_1$–$C_6$-alkyl-saturated 3–8-membered cycloalkyl, and $C_1$–$C_6$-alkyl-unsaturated 3–8-membered cycloalkyl.

2. The pharmaceutical composition according to claim 1, wherein X is $NOR^6$ and $R^6$ is selected from the group consisting of H, $C_1$–$C_6$ alkyl, $C_2$–$C_6$ alkenyl, $C_2$–$C_6$ alkynyl, acyl, aryl, saturated or unsaturated 3–8-membered cycloalkyl, and $C_1$–$C_6$-alkyl aryl, wherein said cycloalkyl or aryl groups may be fused with 1–2 cycloalkyl or aryl groups.

3. The pharmaceutical composition according to claim 2, wherein $R^6$ is H or $CH_3$.

4. The pharmaceutical composition according to any claim 1, wherein $R^1$ is a $C_1$–$C_6$-alkyl, $C_2$–$C_6$-alkenyl, $C_2$–$C_6$-alkynyl, aryl, saturated or unsaturated 3–8-membered cycloalkyl.

5. The pharmaceutical composition according to claim 4, wherein $R^1$ is a biphenyl.

6. The pharmaceutical composition according to claim 1, wherein X is $NOR^6$, $R^6$ is H, a $C_1$–$C_6$-alkyl, or aryl or $C_1$–$C_6$-alkyl aryl group and $R^1$ is selected from $C_1$–$C_6$-alkyl; aryl or $C_1$–$C_6$-alkyl aryl.

7. The pharmaceutical composition according to claim 6, wherein $R^6$ is methyl, R is a $C_1$–$C_6$-alkyl group and $R^1$ is a biphenyl.

8. A method of modulating an oxytocin receptor in vitro comprising administering to one or more cells having an oxytocin receptor the pharmaceutical composition according to claim 1.

9. The method according to claim 8, wherein said modulating comprises blocking the oxytocin receptor or in antagonising the binding of oxytocin to its receptor.

10. A method of treating premature labor, premature birth or dysmenorrheal comprising administering to a patient in need thereof an effective amount of the pharmaceutical composition of claim 1.

11. A pyrrolidine ester compound of formula (I'), or a pharmaceutically acceptable salt thereof,

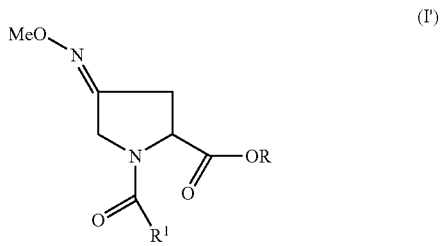

(I')

wherein R is selected from $C_1$–$C_6$ alkyl, $C_1$–$C_6$ alkyl aryl, and 3–8-membered cycloalkyl and $R^1$ is selected from the group consisting of a 1,1'-biphenyl, a pyridinyl-phenyl and a pyrimidinyl-phenyl group.

12. A pyrrolidine ester compound according to claim 11, wherein R is a methyl group.

13. A pyrrolidine ester compound according to claim 11, wherein $R^1$ is a 1,1'-biphenyl group.

14. A pyrrolidine ester compound according to claim 11, wherein $R^1$ is a 1,1'-biphenyl group which is substituted by 1 or 2 substituents selected from the group consisting of $C_1$–$C_6$ alkyl, $C_1$–$C_6$ alkoxy, halogen, CN.

15. A pyrrolidine derivative according to claim 11, selected from the group consisting of:
Methyl (2S,4EZ)-4-(methoxyimino)-1-[(2'-methyl[1,1'-biphenyl]-4-yl)carbonyl]-2-pyrrolidinecarboxylate,
Methyl (2S,4EZ)-1-([1,1'-biphenyl]-4-ylcarbonyl)-4-(methoxyimino)-2-pyrrolidinecarboxylate,
Methyl (2S,4E)-4-(methoxyimino)-1-[(2'-methyl[1,1'-biphenyl]-4-yl)carbonyl]-2-pyrrolidinecarboxylate,
Methyl (2S,4Z)-4-(methoxyimino)-1-[(2'-methyl[1,1'-biphenyl]-4-yl)carbonyl]-2-pyrrolidinecarboxylate,
Methyl (2S,4EZ)-1-[(2'-fluoro[1,1'-biphenyl]-4-yl)carbonyl]-4-(methoxyimino)-2-pyrrolidinecarboxylate,
Methyl (2S,4Z)-1-[(2'-fluoro[1,1'-biphenyl]-4-yl)carbonyl]-4-(methoxyimino)-2-pyrrolidinecarboxylate,
Methyl (2S,4EZ)-1-[(2'-chloro[1,1'-biphenyl]-4-yl)carbonyl]-4-(methoxyimino)-2-pyrrolidinecarboxylate,
Methyl (2S,4EZ)-1-[(2'-cyano[1,1'-biphenyl]-4-yl)carbonyl]-4-(methoxyimino)-2-pyrrolidinecarboxylate,
Methyl (2S,4EZ)-4-(methoxyimino)-1 {[2'-(trifluoromethyl)[1,1'-biphenyl]-4-yl]carbonyl}-2-pyrrolidinecarboxylate,
Methyl (2S,4EZ)-1-[(2'-methoxy[1,1'-biphenyl]4-yl)carbonyl]-4-(methoxyimino)-2-pyrrolidinecarboxylate,
Methyl (2S,4EZ)-1-[(2',6'-dimethyl[1,1'-biphenyl]-4-yl)carbonyl]-4-(methoxy-imino)-2-pyrrolidinecarboxylate,
Methyl (2S,4EZ)-1-[(2',3-dimethyl[1,1'-biphenyl]4-yl)carbonyl]-4-(methoxy-imino)-2-pyrrolidinecarboxylate,
Methyl (2S,4EZ)-1-[(3-methyl[1,1'-biphenyl]-4-yl)carbonyl]4-(methoxyimino)-2-pyrrolidinecarboxylate,
Methyl (2S,4EZ)-1-[(3',4'-dichloro[1,1'-biphenyl]-4-yl)carbonyl]-4-(methoxy-imino)-2-pyrrolidinecarboxylate,
Ethyl (2S,4EZ)-1-([1,1'-biphenyl]-4-ylcarbonyl)-4-(methoxyimino)-2-pyrrolidinecarboxylate,
sec-butyl (2S,4EZ)-4-(methoxyimino)-1-[(2'-methyl[1,1'-biphenyl]-4-yl)carbonyl]2-pyrrolidinecarboxylate,
Cyclopentyl (2S,4EZ)-4-(methoxyimino)-1-[(2'-methyl[1,1'-biphenyl]-4-yl)carbonyl]-2-pyrrolidinecarboxylate, and
Methyl (2S,4EZ)-1-[(4'-fluoro[1,1'-biphenyl]-4-yl)carbonyl]4-(methoxyimino)-2-pyrrolidinecarboxylate.

16. A pharmaceutical composition comprising at least one pyrrolidine derivative according to claim 11, and a pharmaceutically acceptable carrier, diluent or excipient thereof.

17. A process of preparing a compound according to claim 11, comprising:
reacting a compound of formula (III)

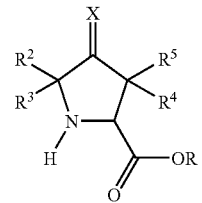

wherein X, $R^2$–$R^5$ are H,
with a carboxylic acid or acyl chloride of formulae (IVa) or (IVb)

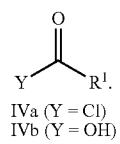

IVa (Y = Cl)
IVb (Y = OH)

18. The pharmaceutical composition of claim 11, wherein R is a methyl group.

19. A method of treating and/or preventing premature labor, premature birth or dysmenorrheal, comprising administering to a patient in need thereof an effective amount of the pharmaceutical composition of claim 1.

* * * * *